United States Patent
Armani et al.

(10) Patent No.: US 9,116,128 B2
(45) Date of Patent: *Aug. 25, 2015

(54) CLICK CHEMISTRY SURFACE FUNCTIONALIZATION FOR RESONANT MICRO-CAVITY SENSORS

(75) Inventors: Andrea M. Armani, Pasadena, CA (US); Akinleye C. Alabi, Pasadena, CA (US); Mark E. Davis, Pasadena, CA (US); Richard C. Flagan, Pasadena, CA (US); Scott E. Fraser, La Canada, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/346,484

(22) Filed: Jan. 9, 2012

(65) Prior Publication Data

US 2012/0107177 A1  May 3, 2012

Related U.S. Application Data

(63) Continuation of application No. 12/324,605, filed on Nov. 26, 2008, now Pat. No. 8,092,855.

(60) Provisional application No. 61/004,580, filed on Nov. 28, 2007.

(51) Int. Cl.
*G01N 33/547* (2006.01)
*G01N 33/553* (2006.01)
*G01N 33/543* (2006.01)
*G01N 21/77* (2006.01)

(52) U.S. Cl.
CPC ...... *G01N 21/7746* (2013.01); *G01N 33/54353* (2013.01); *G01N 2021/7789* (2013.01)

(58) Field of Classification Search
CPC .................. G01N 21/7746; G01N 2021/7789; G01N 33/54353
See application file for complete search history.

(56) References Cited

U.S. PATENT DOCUMENTS

| 3,589,794 A | 6/1971 | Marcatili |
| 3,760,297 A | 9/1973 | Thompson |
| 4,282,499 A | 8/1981 | DeFonzo |

(Continued)

FOREIGN PATENT DOCUMENTS

| FR | 2703473 | 10/1994 |
| JP | 05203826 | 8/1993 |

(Continued)

OTHER PUBLICATIONS

Chao et al. Polymer microring resonators for biochemical sensing applications. IEEE Journal 2006, vol. 12, No. 1, pp. 134-142.*

(Continued)

*Primary Examiner* — Shafiqul Haq
(74) *Attorney, Agent, or Firm* — Vista IP Law Group LLP; Gary D. Lueck

(57) ABSTRACT

Micro-cavity resonant sensors have outer surfaces that are functionalized using click chemistry, e.g., involving a cycloaddition reaction of an alkyne functional group and an azide functional group. A first polymer linking element binds to an outer surface of the micro-cavity and has an azide functional group, which bonds to an alkyne functional group of a second polymer linking element as a result of a cycloaddition reaction. A functionalization element such as an antibody, antigen or protein for sensing a target molecule is bound to the second linking element.

21 Claims, 28 Drawing Sheets

(56) References Cited

U.S. PATENT DOCUMENTS

| | | | |
|---|---|---|---|
| 4,695,121 | A | 9/1987 | Mahapatra et al. |
| 5,343,490 | A | 8/1994 | McCall |
| 5,878,070 | A | 3/1999 | Ho et al. |
| 6,052,495 | A | 4/2000 | Little et al. |
| 6,078,605 | A | 6/2000 | Little et al. |
| 6,101,300 | A | 8/2000 | Fan et al. |
| 6,222,964 | B1 | 4/2001 | Sadot et al. |
| 6,259,717 | B1 | 7/2001 | Stone et al. |
| 6,490,039 | B2 | 12/2002 | Maleki et al. |
| 6,657,731 | B2 | 12/2003 | Tapalian et al. |
| 7,226,733 | B2 * | 6/2007 | Chan et al. ............... 435/6.19 |
| 7,693,369 | B2 * | 4/2010 | Fan et al. .................. 385/32 |
| 8,092,855 | B2 * | 1/2012 | Armani et al. ............. 427/2.13 |
| 2001/0033587 | A1 | 10/2001 | Vahala et al. |
| 2002/0018611 | A1 | 2/2002 | Maleki et al. |
| 2002/0080842 | A1 | 6/2002 | An et al. |
| 2002/0192680 | A1 | 12/2002 | Chan et al. |
| 2003/0021518 | A1 | 1/2003 | Smirnov et al. |
| 2004/0179573 | A1 | 9/2004 | Armani et al. |
| 2007/0269901 | A1 * | 11/2007 | Armani et al. ............. 436/172 |

FOREIGN PATENT DOCUMENTS

| | | |
|---|---|---|
| WO | 9805995 | 2/1998 |
| WO | 0140757 | 6/2001 |

OTHER PUBLICATIONS

Lin et al. Surface modification of magnetic nanoparticle via Cu(I)-catalyzed alkyne-azide [2+3] cycloaddition. Organic Letters 2007, vol. 9, No. 11, pp. 2131-2134.*

Fleming et al. Trizole cycloaddition as a general route for functionalization of Au Nanoparticle. Chem. Mater. 2006, vol. 18, pp. 2327-2334.*

Armani, D., et al, "Ultra-high-Q toroid microcavity on a chip," Nature 421:925-927 (Feb. 27, 2003).

Bumki, M., et al., "Compact, fiber-compatible, cascaded Raman laser," Optics Letters 28(17) (Sep. 1, 2003).

Cai, M. et al., "Observation of critical coupling in a fiber taper to a silica-microsphere whispering gallery mode system," Physical Review Letters 85(1):74-77 (Jul. 3, 2000).

Cai, M., et al., "Fiber coupled microsphere laser," Optics Letters 25(10):1430-1432 (Oct. 1, 2000).

Chan, Isaac W.T., "Gas phase pulse etching of silicon for MEMS with xenon diflouride," IEEE, 0-7803-5579-2:1637-1642 (May 1999).

Chin, M., et al., "Design and modeling of waveguide-coupled single-mode micoring resonators," Journal of Lightwave Technology, 16(8):1433-1446 (Aug. 1998).

Chu, S.T. et al., "An eight-channel add-drop filter using vertically coupled microring resonators over a cross grid," IEEE Photonics Technology Letters, 11(6):691-693 (Jun. 1999).

Djordjev, K., "Vertically coupled InP microdisk switching devices with electroabsorptive active regions," IEEE Photonics Technology Letters 14(8):1115-1117 (Aug. 2002).

Djordjev, K., "Microdisk tunable resonant filters and switches," IEEE Photonics Technology Letters 14(6):828-830 (Jun. 2002).

Gayral, B., et al., "High-Q wet-etched GaAs microdisks containing inAs quantum boxes," Applied Physics Letters 75 (13):1908-1910 (Sep. 27, 1999).

Gerard, J. M., et al., "Quantum boxes as active probes for photonic microstructures: The pillar microcavity case," Applied Physics Letters 69(4):449-451 (Jul. 22, 1996).

Gorodetsky, M.L., et al, "Ultimate Q of optical microsphere resonators," Optics Letters 21(7):453-455 (Apr. 1, 1996).

Grover, R., et al., "Parallel-cascaded semiconductor microring resonators for high-order and wise-FSR filters," Journal of Lightwave Technology, 20(5):900-905 (May 2002).

Kawachi, M., "Silica waveguide on silicon and their applications to integrated-optic components," Optical and Quantum Electronics 22:391-416 (1990).

Kippenberg, S.M., et al., "Fabrication and coupling to planar high-Q silica disk mocrocavities," Applied Physics Letters 83(4):797-799 (Jul. 28, 2003).

Knight, J.C., "Phase-matched exitation of whispering-gallery-mode resonances by a fiber taper," Optics Letters 22 (15):1129-1131 (Aug. 1, 1997).

Krioukov, E., et al., "Sensor based on an integrated optical microcavity," Optics Letters 27(7)512-514 (Jan. 1, 2002).

Little, B.E., et al., "Microring resonator channel dropping filters," Journal of Lightwave Technology 15(6):998-1005 (Jun. 1997).

Little, B. E., et al., "Vertically coupled glass microring resonator channel dropping filters," IEEE Photonics Technology Letters 11(2):215-217 (Feb. 1999).

Little, B.E., et al., "Wavelength switching and routing using absorption and resonance," IEEE Photonics Technology Letters 10(6):816-818 (Jun. 1998).

McCall, S. L., et al., "Whispering-gallery mode microdisk lasers," Applied Physics Letters, 60(3):289-291 (Jan. 20, 1992).

Michler, P., et al., "Quantum dot lasers using high-Q microdisk cavities," Physica Status Solidi B-Basic Research 224:797-801 (2001).

Offrein, B.J., et al., "Resonant coupler-based tunable add-after-drop filter in silicon-oxynitride technology for WDM networks," IEEE Journal of Selected Topics in Quantum Electronics 5(5):1400-1406 (Sep.-Oct. 1999).

Rabiei Payam, et al., "Polymer micro-ring filters and modulators," Journal of Lightwave Technology 20 (11):1968-1975 (Nov. 11, 2002).

Sandoghdar, V. et al., "Very low threshold whispering-gallery-mode microsphere laser," Physical Review A, 54(3): R1777-R1780 (Sep. 1996).

Schiller, S., et al., "Fused-silica monolithic total-internal-reflection resonator," Optics Letters 17(5):378-380 (Mar. 1, 1992).

Spillane, S.M., et al., "Ultralow-threshold Raman laser using a spherical dielectric microcavity," Nature 415:621-623 (Feb. 7, 2002).

Yanagase, Y., et al., "Box-like filter response and expansion of FSR by a vertically triple coupled microring resonator filter," Journal of Lightwave Technology 20(8):1525-1529 (Aug. 2002).

Yang, L., et al., "Gain functionalization of silica microresonators," Optics Letters 28(8) (Apr. 15, 2003).

Yang, L., et al., "Fiber-coupled erbium microlasers on a chip," Applied Physics Letters 83(5):825-826 (Aug. 4, 2003).

Yariv, A., "Universal relations for coupling of optical power between microresonators and dielectric waveguides," Electronics Letters 36(4):321-322 (Jan. 17, 2000).

Vemooy, D.W., et al., "High-Q measurements of fused silica microspheres in the near infrared," Optics Letters 23 (4):247-249 (Feb. 15, 1998).

Vollmer, F., et al., "Protein detection by optical shift of a resonant microcavity," Applied Physics Letters 80(21) (May 27, 2002).

Von Klitzing, W., et al., "Tunable whispering gallery modes for spectroscopy and CQED experiments," New Journal of Physics 3:14.1-14.4 (Aug. 3, 2001).

International Search Report mailed 3/26/20005, in international Application No. PCT/US03/31727, filed Oct. 2, 2003.

Office Actions mailed Dec. 10, 2007, Jul. 10, 2008, Jan. 8, 2009, and Jul. 16, 2009, Notice of Allowance mailed Apr. 14, 2010, and Issue Notification mailed Aug. 4, 2010, in U.S. Appl. No. 11/733,480, filed Apr. 10, 2007.

Office Action mailed Oct. 13, 2005, Feb. 12, 2007, Apr. 30, 2007, Oct. 19, 2007, Notice of Allowance mailed Feb. 27, 2009, and Issue Notification mailed May 20, 2009, in U.S. Appl. No. 10/678,354, filed Oct. 2, 2003.

Yang, Tianzhong et al., "Nanoparticles for Biomedical Applications" in "Micro and Nano Manipulations for Biomedicai Applications" Chapter 3, 2008 (58 pages).

O'Reilly, Rachel et al., "Functionalization of Miscelles and Shell Corss-linked Nanoparticles Using Click Chemistry" dated Sep. 28, 2005, American Chemical Society, Chem. Mater. 2005, 17, 5976-5988 (13 pages).

http://en.wikipedia.org/wiki/Molecular_mass, printed Apr. 29, 2014 (3 pages).

http://en.wikipedia.org/wiki/Molecular_mass, printed Apr. 29, 2014 (8 pages).

* cited by examiner

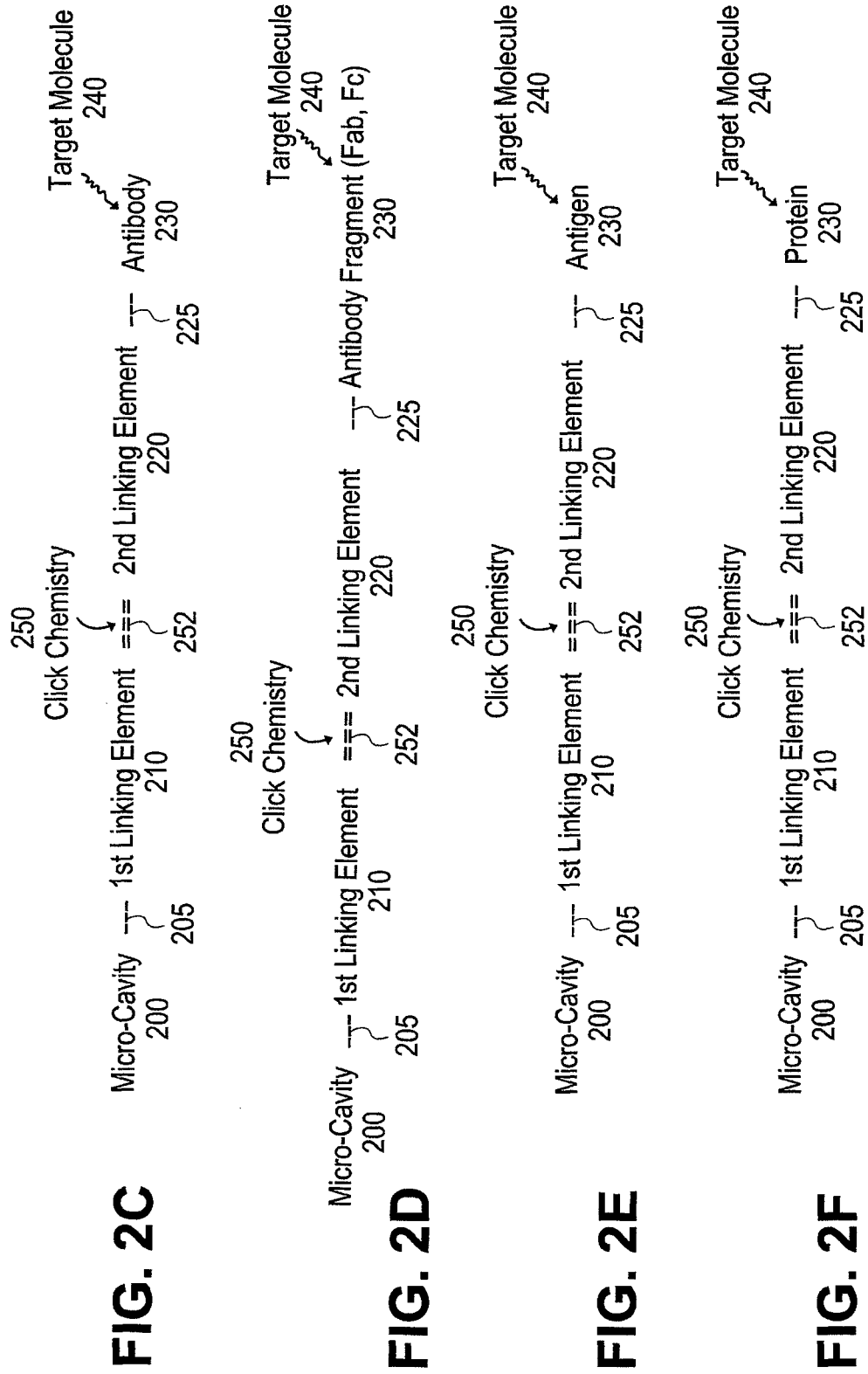

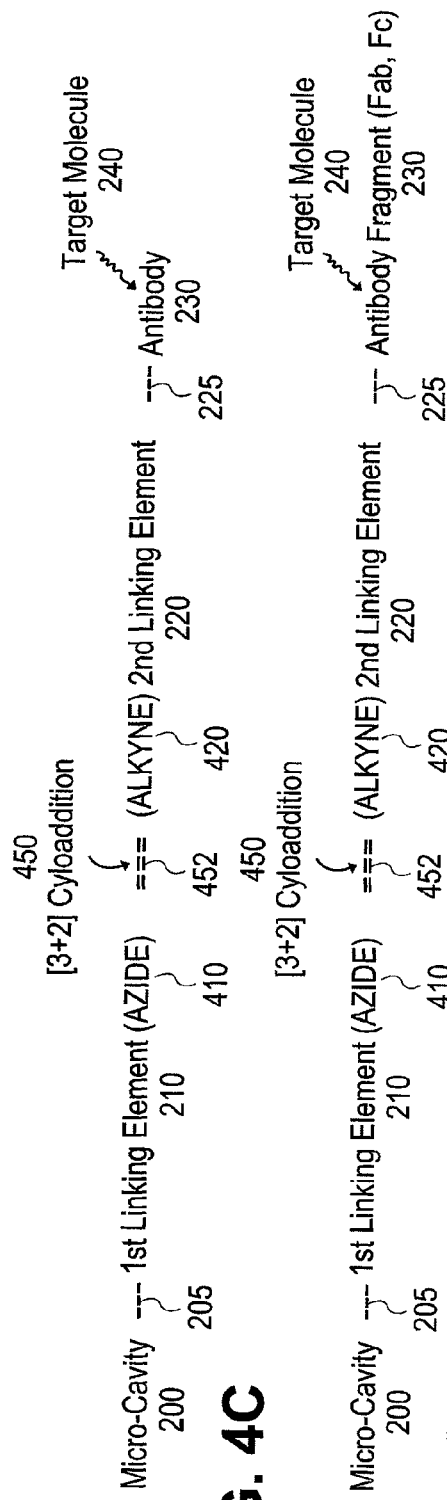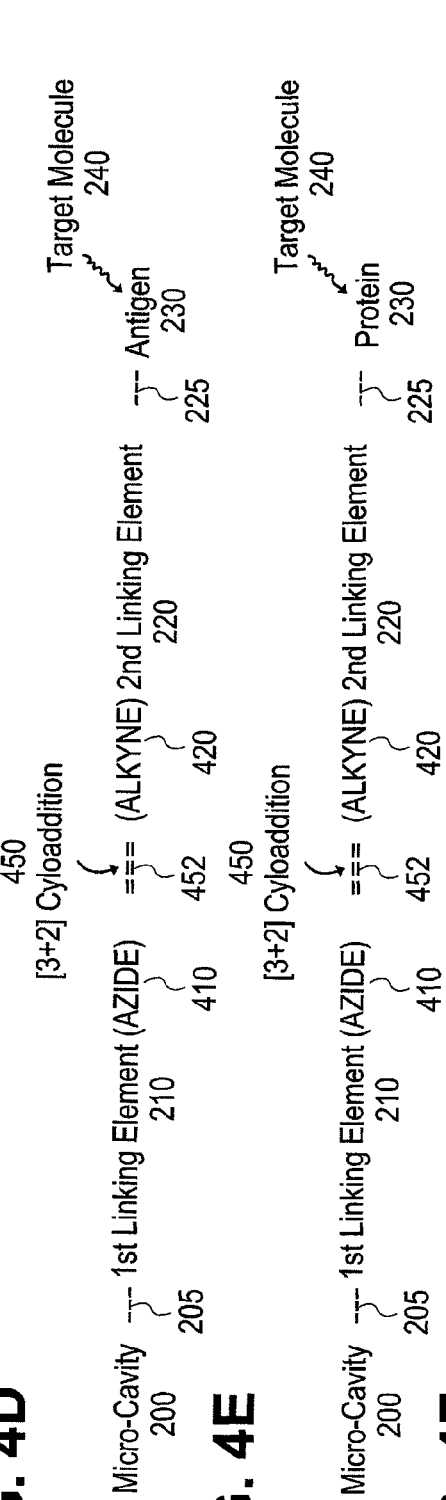
FIG. 4C
FIG. 4D
FIG. 4E
FIG. 4F

TRITC

MAL-PEG$_{24}$-NHS

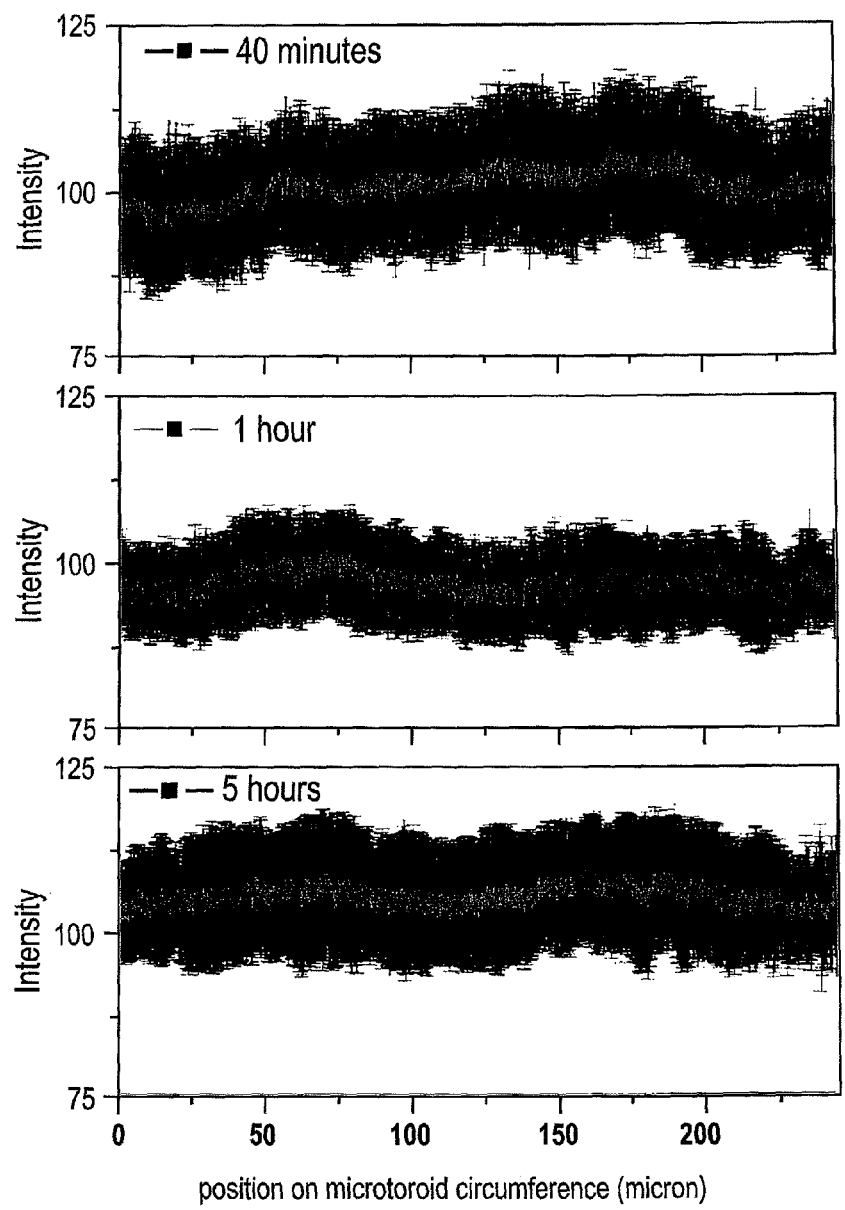
FIG. 21C (Sample 3)
FIG. 21B (Sample 2)
FIG. 21A (Sample 1)

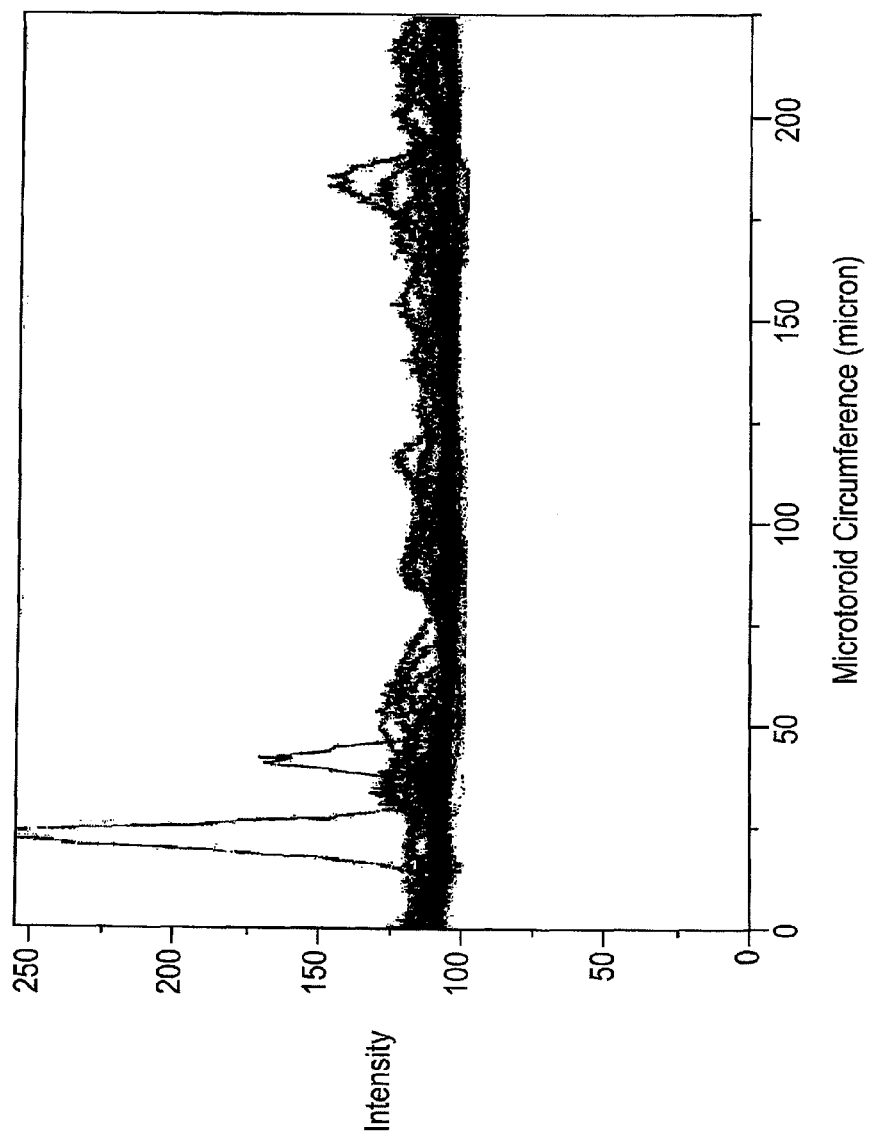

CLICK CHEMISTRY SURFACE FUNCTIONALIZATION FOR RESONANT MICRO-CAVITY SENSORS

RELATED APPLICATION DATA

The present application is a continuation of U.S. patent application Ser. No. 12/324,605, filed on Nov. 26, 2008, which claims the benefit under 35 U.S.C. §119 of U.S. Provisional Patent Application Ser. No. 61/004,580, filed on Nov. 28, 2007, the contents of which are incorporated herein by reference as though set forth in full.

This application may also be related to the following applications and patent, the contents of which are also incorporated herein by reference as though set forth in full: U.S. application Ser. No. 12/243,580, filed on Oct. 1, 2008; U.S. application Ser. No. 11/733,480, filed on Apr. 10, 2007; U.S. application Ser. No. 11/016,067, filed on Dec. 17, 2004; and U.S. application Ser. No. 10/678,354, filed on Oct. 2, 2003, and U.S. Pat. No. 6,583,399, issued on Jun. 24, 2003.

STATEMENT REGARDING FEDERALLY SPONSORED RESEARCH

The U.S. Government has certain rights in this invention pursuant to Grant No. HR 0011-04-1-0032 awarded by DARPA.

FIELD OF INVENTION

The present invention relates to micro-cavity sensors and sensing methods.

BACKGROUND

Various sensor devices and methods have been utilized to detect target molecules or particulates. Certain sensors involve detection or measurement of biological elements utilizing antibody-antigen interactions. While such sensors may have high specificity, they may have a number of limitations including inadequate sensitivity and the need to utilize labels.

More particularly, certain known sensors require attachment of a label to molecules that are to be detected. This requires prior knowledge of the presence of the target molecule. As a result, known label-based sensor systems are not suitable for blind or label-free detection. Further, use of labels may require additional data processing and ensemble averaging of large numbers of cells. Such processing may confuse or dull recorded responses.

Certain sensors are highly sensitive and capable of detecting a small number of molecules. For example, two known single molecule detection methods include surface enhanced raman spectroscopy (SERS) and total internal reflection fluorescence microscopy (TIRF). However, labels are needed to detect single molecules using these methods. More particularly, a gold surface is used in SERS to amplify a signal corresponding to a single labeled molecule, and with TIRF, a fluorescent label is excited and detected using a single photon camera. Such methods, however, may not be suitable for detecting single molecules in the absence of these labels.

Several sensor devices have been proposed for label-free detection including fiber optic waveguides, nanowires, nanoparticle probes, biochips, mechanical cantilevers and microsphere resonators. Examples of such known devices are described in U.S. Pat. No. 4,071,753 to Fulenwider et al., U.S. Pat. No. 4,419,895 to Fuller and U.S. Pat. No. 6,583,399 to Painter et al. While certain known devices may provide label-free detection capabilities, they have a number of limitations and may not be suitable for various applications and may present integration challenges.

Certain known sensors having functionalized outer surfaces for purposes of selective sensing or detection applications. Such sensors, however, may utilize surface functionalization elements and methods that involve weak bonds that are unable to retain target molecules to the functionalized surface, thereby reducing the effectiveness of the sensor. Other known sensors may have stronger bonds but are silane-based, do not form uniform monolayers, lack high binding efficiency, have limited stability in air or an ambient environment, must be stored in a buffer solution and/or have limited shelf lives and storage restrictions.

SUMMARY

One embodiment is directed to a method for preparing a resonant micro-cavity for use as a sensor, e.g., a label-free sensor. The method comprises functionalizing an outer surface of the surface of the resonant micro-cavity utilizing click chemistry.

Another embodiment is directed to a method for functionalizing a resonant micro-cavity for use as a sensor, e.g., a label-free sensor. The method comprises introducing a first linking element that bonds to an outer surface of the resonant micro-cavity and has a first functional group, and introducing a second linking element having a second functional group. A bond forms between the first functional group and second functional groups as a result of a cycloaddition reaction. The method further comprises introducing a functionalization element for selectively binding a target molecule for sensing or detecting the target molecule, the functionalization element bonding to the second linking element. Embodiments may involve a sequence in which the first linking element binds to the outer surface, the second linking element binds to the first linking element, and the functionalization element binds to the second linking element, or other sequences. For example, in other embodiments, a first linking element binds to the outer surface, and the second linking element, which already has a functionalization element bound thereto, binds to the first linking element. In yet another embodiment, the first linking element, to which a second linking element having an attached functionalization element binds, binds to the outer surface of the micro-cavity.

A further embodiment is directed to a method for functionalizing a resonant micro-cavity for use as a sensor, e.g., a label-free sensor. The method comprises introducing a first polymer linking element that binds to an outer surface of the resonant micro-cavity and has an azide functional group. The first polymer linking element has a molecular weight greater than 100. The method further comprises introducing a second polymer linking element having an alkyne functional group that bonds to the azide functional group of the first polymer linking element as a result of a cycloaddition reaction. The second polymer linking element also has a molecular weight greater than 100. The method further comprises introducing a functionalization element for selectively binding a target molecule to enable sensing or detection of the target molecule, the functionalization element bonding to the second linking element.

According to another embodiment, a resonant micro-cavity sensor comprises a resonant micro-cavity, first and second linking elements, and a functionalization element for sensing a target molecule. The resonant micro-cavity has an outer surface to which the first linking element is bound. The second linking element is bound to the first linking element by click chemistry, and the functionalization element is bound to the second linking element.

According to yet another embodiment, a resonant micro-cavity sensor comprises a resonant micro-cavity, first and second linking elements having respective first and second functional groups, and a functionalization element for selectively binding a target molecule to enable sensing or detection of the target molecule. The resonant micro-cavity has an outer surface to which the first linking element is bound. A bond is formed between the first functional group and the second functional group as a result of a cycloaddition reaction, and the functionalization element is bound to the second linking element.

In accordance with a further alternative embodiment, a resonant micro-cavity sensor comprises a resonant micro-cavity, first and second polymer linking elements, and a functionalization element, which provides for selectively binding a molecule for detecting or sensing the molecule. The resonant micro-cavity has an outer surface to which a first polymer linking element having a molecular weight greater than 100 and an azide functional group is bound. The second polymer linking element has a molecular weight greater than 100 and an alkyne functional group. The azide and alkyne functional groups bond to each other as a result of a cycloaddition reaction. The functionalization element is bound to the second polymer linking element.

A further embodiment is directed to a method for detecting or sensing a target molecule. The method comprises introducing optical energy into a resonant micro-cavity having an outer surface that is functionalized utilizing click chemistry. The method further comprises sensing or detecting the target molecule based on or as a result of a change of an optical property of optical energy resonating within the micro-cavity.

Another embodiment is directed to method for detecting or sensing a target molecule. The method comprises introducing optical energy into a resonant micro-cavity having an outer surface that is functionalized by introducing a first linking element that bonds to the outer surface of the resonant micro-cavity and has a first functional group, introducing a second linking element having a second functional group, a bond forming between the first functional group and second functional groups as a result of a cycloaddition reaction. The method further comprises introducing a functionalization element for selectively binding a target molecule for detecting or sensing the target molecule, the functionalization element bonding to the second linking element. The method further comprises detecting the target molecule based on or as a result of a change of an optical property of optical energy resonating within the micro-cavity.

A further alternative embodiment is directed to a method for detecting a target molecule and comprises introducing optical energy into a resonant micro-cavity having an outer surface that is functionalized by introducing a first polymer linking element that bonds to an outer surface of the resonant micro-cavity and has an azide functional group, the first polymer linking element having a molecular weight greater than 100. The method further comprises introducing a second polymer linking element having an alkyne functional group that bonds to the azide functional group of the first polymer linking element as a result of a cycloaddition reaction, the second polymer linking element having a molecular weight greater than 100, and introducing a functionalization element for sensing a target molecule, the functionalization element bonding to the second linking element. The method further comprises sensing or detecting the target molecule based on or as a result of a change of an optical property of optical energy resonating within the micro-cavity.

In one or more embodiments, a first linking element bonds to the outer surface of the resonant micro-cavity and the second linking element bonded thereto form a single substantially uniform layer. A first linking element and a second linking element are covalently bonded to each other by click chemistry, e.g., by cycloaddition of an azide group of the first linking element and an alkyne group of the second linking element.

In at least one embodiment, a functionalization element for selecting binding a target molecule to enable detection or sensing of the target molecule is bound to a second linking element and may be an antibody, an antibody fragment, an antigen or a protein for use in detecting various target molecules.

In one or more embodiments, one or more linking elements are made of a polymer, such as polyethylene glycol (PEG), polyethylene oxide (PEO) or another suitable polymer, e.g., a polymer having a molecular weight greater than 100. For example, the molecular weight of a polymer chain of the first linking element may be greater than about 300, and a molecular weight of a polymer chain of the second linking element may be greater than 1500.

In at least one embodiment, the micro-cavity of a sensor or that is involved in a functionalization or sensing method may be various shapes, be made of different materials and have various Q values. In certain embodiments, the micro-cavity is made of silica and is planar, e.g., a silica toroid-shaped micro-cavity. In certain embodiments, a substrate may support the micro-cavity, such as a toroid-shaped or other planar micro-cavity, and an outer edge of the resonant micro-cavity extends outwardly beyond a top of the substrate. In other embodiments, the micro-cavity is a spheroid or micro-sphere.

In one or more embodiments, the micro-cavity has a Q factor much greater than $10^6$, e.g., greater than $10^8$. With embodiments, high or ultra-high Q factors provide high sensitivity and provide for the ability to detect a small number of molecules and even an individual molecule while the functionalized outer surface provides for high specificity.

BRIEF DESCRIPTION OF THE DRAWINGS

The foregoing and other aspects of embodiments will understood with reference to the detailed description of illustrated embodiments in conjunction with the accompanying drawings, wherein:

FIGS. 2C-F illustrate bonding of different components, linking elements and functionalization elements that may be utilized in embodiments illustrated in FIGS. 2A-B, wherein FIG. 2C illustrates use of an antibody functionalization element, FIG. 2D illustrates use of an antibody fragment functionalization element, FIG. 2E illustrates use of an antigen functionalization element, and FIG. 2F illustrates use of a protein functionalization element;

FIGS. 4C-F illustrates bonding of different components, linking elements and functionalization elements that may be utilized in embodiments illustrated in FIGS. 4A-B, wherein FIG. 4C illustrates use of an antibody functionalization element, FIG. 4D illustrates use of an antibody fragment functionalization element, FIG. 4E illustrates use of an antigen functionalization element, and FIG. 4F illustrates use of a protein functionalization element;

FIGS. 21A-C are graphs further illustrating fluorescence intensity test results of bonding of fluorescently labeled counterparts to a first linking element as shown in FIG. 19 and that were synthesized using three different methods;

FIGS. 23A-C are graphs illustrating fluorescence intensity test results and data of bonding of the fluorescently labeled counterpart shown in FIG. 22 to different circumferential positions on the outer surface of the micro-cavity;

FIGS. 25A-B are graphs illustrating Q factor tests utilizing the resonant micro-cavities functionalized as shown in FIG. 24, wherein FIG. 25A illustrates Q factor data for a number of different micro-cavities before and after attachment of the first linking element having the azide functional group, and FIG. 25B illustrates Q factor data for a number of different micro-cavities before and after attachment of both of the first and second linking elements.

DETAILED DESCRIPTION OF ILLUSTRATED EMBODIMENTS

Figure 1:
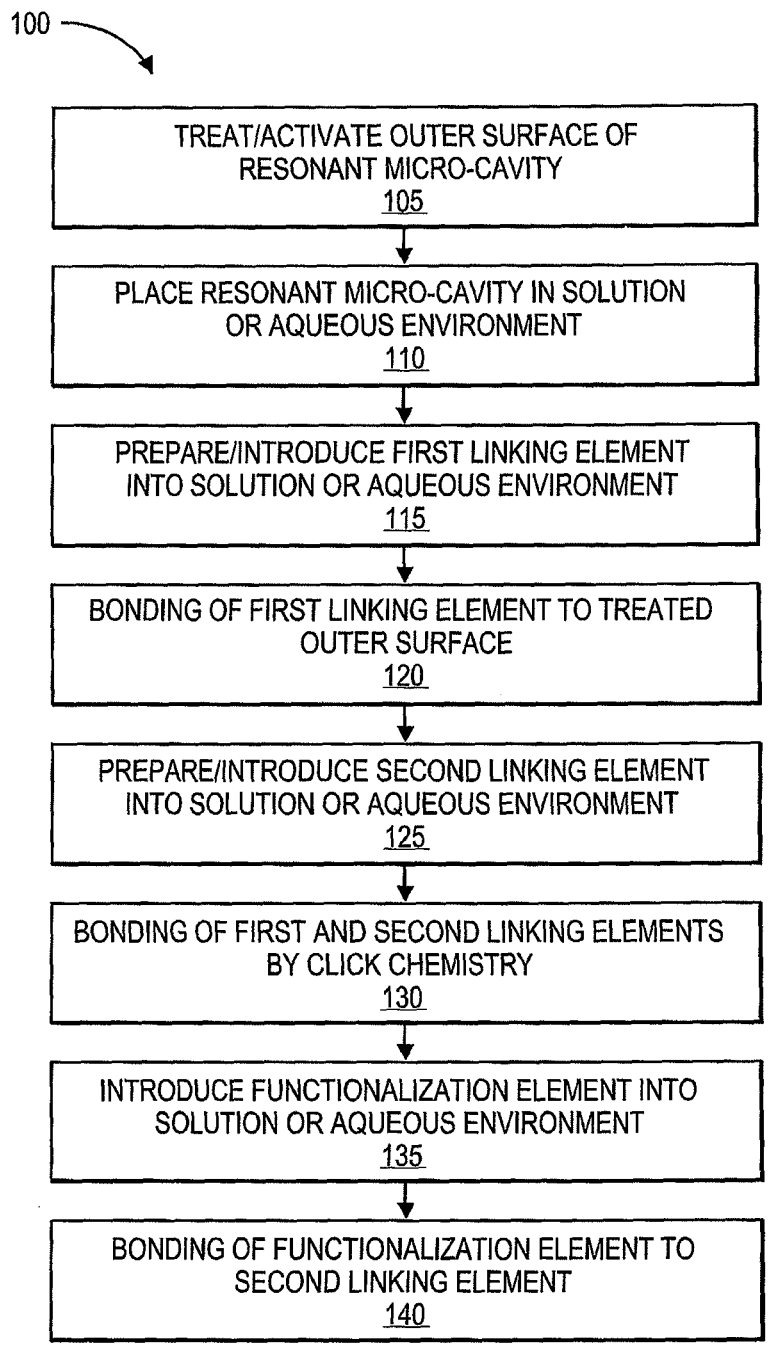
FIG. 1 is a flow chart of a method for functionalizing an outer surface of a resonant micro-cavity using click chemistry according to one embodiment.

Embodiments of the invention are related to methods for functionalizing a surface of a resonant micro-cavity for use as a sensor and resulting resonant micro-cavity sensors having a functionalized surface and label-free or blind detection or sensing methods, including label-free or blind detection or sensing of single or individual molecules. Surface functionalization embodiments are based on or utilize click chemistry, e.g., the [3+2]cycloaddition reaction (also referred to as a [1+3] cylcoaddition reaction) of an azide functional group and an alkyne functional group. For example, an azide functional group of a first linking element that binds or bonds to an outer surface of a resonant micro-cavity and an alkyne of a second linking element to which a functionalization element for detecting a target molecule is attached are bonded together by click chemistry or a cycloaddition reaction.

"Click chemistry" as utilized in this specification is defined as a chemical reaction involving molecular building blocks that selectively and covalently bond or "click" together. A "cycloaddition" reaction as utilized in this specification is defined as a type of click chemistry reaction One embodiment of the invention utilizes a 1+3-dipolar cycloaddition reaction of azide and alkyne functional groups, otherwise referred to as a [3+2]cycloaddition reaction. Other embodiments may involve other reactions including, for example, the Diels-Alder [4+2] cylcoaddition reaction between a diene and a dienophile. For ease of explanation, reference is made to click chemistry or a [3+2]cycloaddition reaction.

Resonant micro-cavity sensors that are functionalized according to embodiments have high sensitivity as a result of high or ultra-high Q values and high selectivity as a result of surface functionalization by click chemistry or cycloaddition reactions. Sensor embodiments also provide for uniform, high-density covalent surface immobilization of molecules and high binding efficiencies. Such sensors also have improved environmental stability (e.g., temperature and pH) as a result of covalent bonds that provide for temperature and pH changes to controllably release target molecules and for repeat sensor use. Micro-cavity surfaces functionalized according to embodiments are also less susceptible to chemical degradation such as oxidative processes and are stable in air. This allows sensor embodiments to be stored for longer durations and for storage flexibility. Further, given the manner in which micro-cavity surfaces are functionalized with a non-naturally occurring azide functional group, embodiments do not involve incorrect binding of naturally occurring or biological elements to unbound azide functional groups, which may otherwise occur in known devices that involve incorrect binding of biological elements and associated impaired sensor performance.

Multiple sensors having surfaces functionalized according to embodiments may form an array of sensors, and sensors in an array may have diameters, materials, shapes, Q values and functionalization elements to provide different or customized detection capabilities and detection of different target molecules. Sensors and arrays thereof may also be configured for integration on a chip and in a sampling and concentration system. Embodiments can be utilized in continuous, real-time monitoring applications and detection of particles and molecules in a solution or in air when utilizing a suitable condenser. Further, embodiments may be used in, for example, military applications, commercial and research applications including but not limited to explosives detection, process controls, cell signaling and single molecule studies, environmental monitoring, chemical detection, toxicology, medical diagnostics and other applications.

Further aspects of embodiments and applications thereof are described in further detail with reference to FIGS. 1-4F. Micro-cavities that can be functionalized according to embodiments, methods of fabrication, and detection systems in which such micro-cavity sensors may be integrated are described with reference to FIGS. 5-10. Embodiments involving a toroid-shaped resonant micro-cavity and tests thereof are described in further detail with reference to FIGS. 11-25B.

Referring to FIG. 1 and with further reference to FIGS. 2A-F, a method 100 for preparing or functionalizing a resonant micro-cavity 200 in which optical energy 260 resonates for use as a sensor (generally referred to as resonant micro-cavity or sensor 200) involves click chemistry 250, a first linking element 210 that binds or bonds to an outer surface 202 of the micro-cavity 200, and a second linking element 220 to which a functionalization element 230 is bound. The functionalization element 230 is configured for selectively binding a target molecule to enable detection of the target molecule.

In the illustrated embodiment, the functionalization method 100 involves treating or activating the outer surface 202 of the resonant micro-cavity 200 in preparation for binding or bonding of the first linking element 210 to the outer surface 202 at step 105. According to one embodiment in which the micro-cavity 200 is a silica micro-cavity, step 105 involves treating the outer surface 202 using a Piranha etch solution or other suitable surface treatment. One known Piranha etch solution that may be utilized in embodiments is a mixture of sulfuric acid ($H_2SO_4$) and hydrogen peroxide ($H_2O_2$), e.g., a solution of 70% sulfuric acid ($H_2SO_4$) and 30% hydrogen peroxide ($H_2O_2$). When a micro-cavity 200 is placed in this etch solution, e.g., for about 15 minutes, this solution hydroxylates the outer surface 202 to add OH groups thereto and to activate and prepare the outer surface 202 for binding of the first linking element 210 thereto. The micro-cavity 200 may also be made of other materials including silicon and other suitable materials, and other surface 202 treatments or treatment parameters may be utilized or adjusted as needed. Examples of other reagents or surface treatments that may be utilized with embodiments include, for example, silane-based surface functionalizations (e.g., trimethylcholorsilane and trimethyllorosilane) and plasma-based treatments (e.g., oxygen plasma. This specification refers to a Piranha treatment of a silica micro-cavity surface 202 for ease of explanation.

At step 110, the resonant micro-cavity 200 is placed in a solution or aqueous environment. One example of a solution that may be utilized in embodiments is a phosphate buffered saline solution (PBS) at a pH of about 7.2 to about 7.5. Such a solution may, for example, contain 50-100 mM sodium phosphate (monobasic and dibasic) and 150 mM of NaCl. Another example of a solution that may be utilized is a Tris-HCl buffer or a Citrate-phosphate buffer within the same pH range. For ease of explanation, reference is made generally to a solution or aqueous environment, but it should be understood that various solutions may be utilized.

At step 115, the first linking element 210 is synthesized or prepared (if necessary) and introduced into the solution or aqueous environment in which the resonant micro-cavity 200 is placed. As a result, at step 120, the first linking element 210 binds or covalently bonds 205 to the active or treated outer surface 202 of the silica resonant micro-cavity 200. At step 125, the second linking element 220 is synthesized or prepared (if necessary) and introduced into the solution or aqueous environment. At step 130, a covalent bond 252 is formed between the first linking element 210 and the second linking element 220 by click chemistry 250. Covalent bonds 205, 252 provide for improved environmental (temperature, pH) stability and stability against chemical degradation by processes such as oxidative processes. Embodiments are also better suited for storage and are more flexible compared to other known devices having functionalized outer surfaces with limited storage or shelf lives as a consequence of the biological elements that are utilized to functionalize known devices.

At step 135, a functionalization element 230 for sensing a target molecule 240 that binds 242 to the functionalization element 230 is introduced into the solution or aqueous environment. At step 140, the functionalization element 230 binds or bonds 225 to the second linking element 220. Although FIG. 1 illustrates a certain sequence, it should be understood that steps may occur in different orders or simultaneously.

Figure 2A:
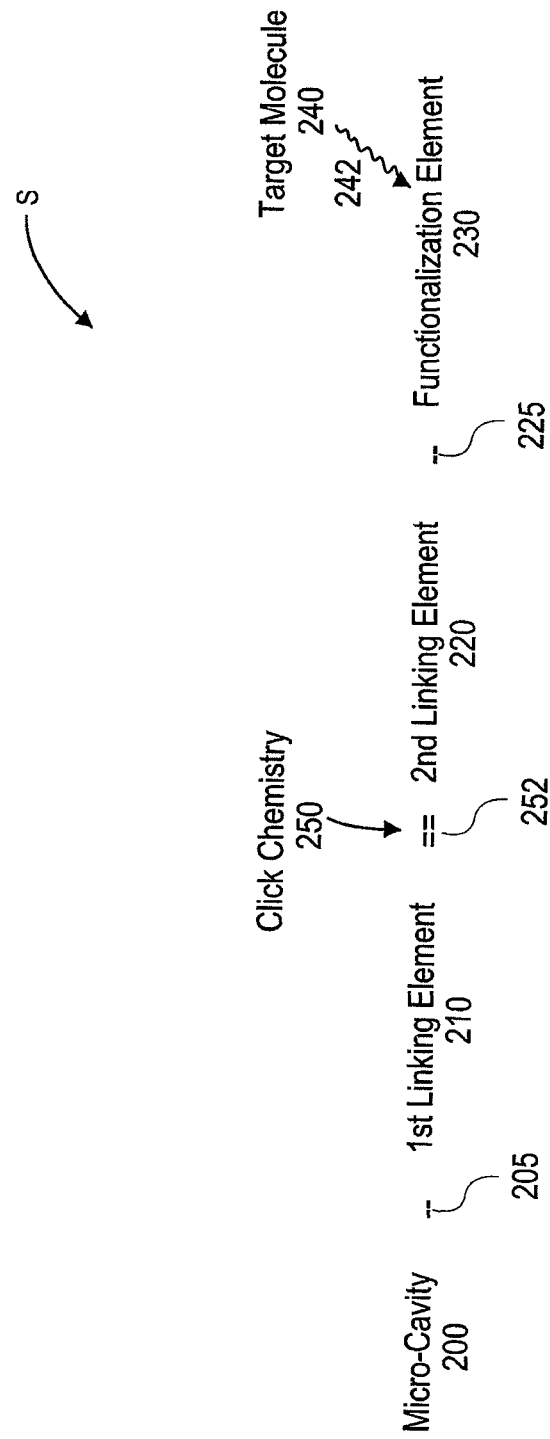
FIG. 2A further illustrates bonding of different components using surface functionalization based on click chemistry.
Figure 2B:
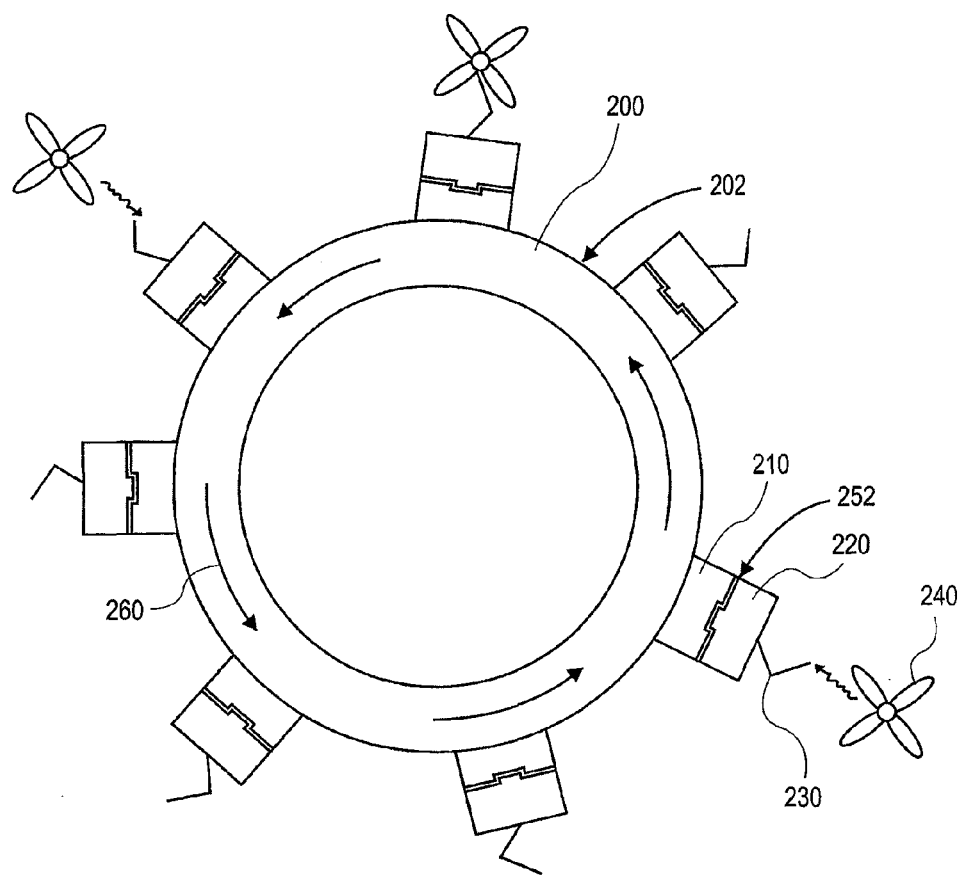
FIG. 2B generally illustrates a top view of a toroid-shaped resonant micro-cavity having an outer surface that is functionalized using click chemistry.

In certain embodiments, the functionalization element 230 as illustrated in FIG. 2A is an antibody (FIG. 2C), an antibody fragment (Fab, Fc) (FIG. 2D); an antigen (FIG. 2E), or a protein (FIG. 2F). Other functionalization elements 230 may also be utilized depending on the target molecule 240 to be detected and/or the method of surface functionalization. Examples of target molecules 240 that may be detected using embodiments include, but are not limited to, DNA, mRNA, virus and bacteria.

A functionalization element 230 or probing element (such as an antibody, antigen, DNA, etc.) can be attached or linked to the second linking element 210 in various ways. For example, the functionalization element 230 usually expresses amines, carboxylic acids and alcohols from its amino acid groups that can be used as points of attachment to the second linking element 220.

In one embodiment, the functionalization element 230 includes amine groups. Different types of bonds and the associated electrophilic agents that may be employed include: Isourea and Isothiourea bonds (Isothiocyanate, Isocyante); Amide and Sulfonamide bonds (Acyl azide, NHS Ester, Sulfonyl chloride, Anhydride, Carbodiimides); Imine and Enamine bonds (reversible Schiff base) (Aldehydes, ketones); secondary amine bond (aldehydes and ketones after reduction with $NaCNBH_3$, epoxides and oxiranes); Carbamate linkage (Carbonates); Arylating agents (Aryl halides); and Amidine Linkage (Imidoesters). In other embodiments, the functionalization element 230 includes carboxylic acid groups that can be coupled via the following bonds and associated electrophilic agents: Ester bonds (Diazoalkanes and Diazoacetyl compounds); Amide bonds (Carbonyldiimidazoles, carbodiimides). In other embodiments, the functionalization element 230 includes hydroxyl groups that can be coupled via the following bonds and associated electrophilic agents: carbamate linkage (carbonyldiimidazole, N,N'-Disuccinimidyl Carbonate (DSC) and N-Hydroxysuccinimidyl chloroformates. Isocyanates) and Ether bonds (Epoxides and Oxiranes). It should be understood that a functionalization element 230 can be attached or bond to the second linking element 220 in various ways.

Figure 3:
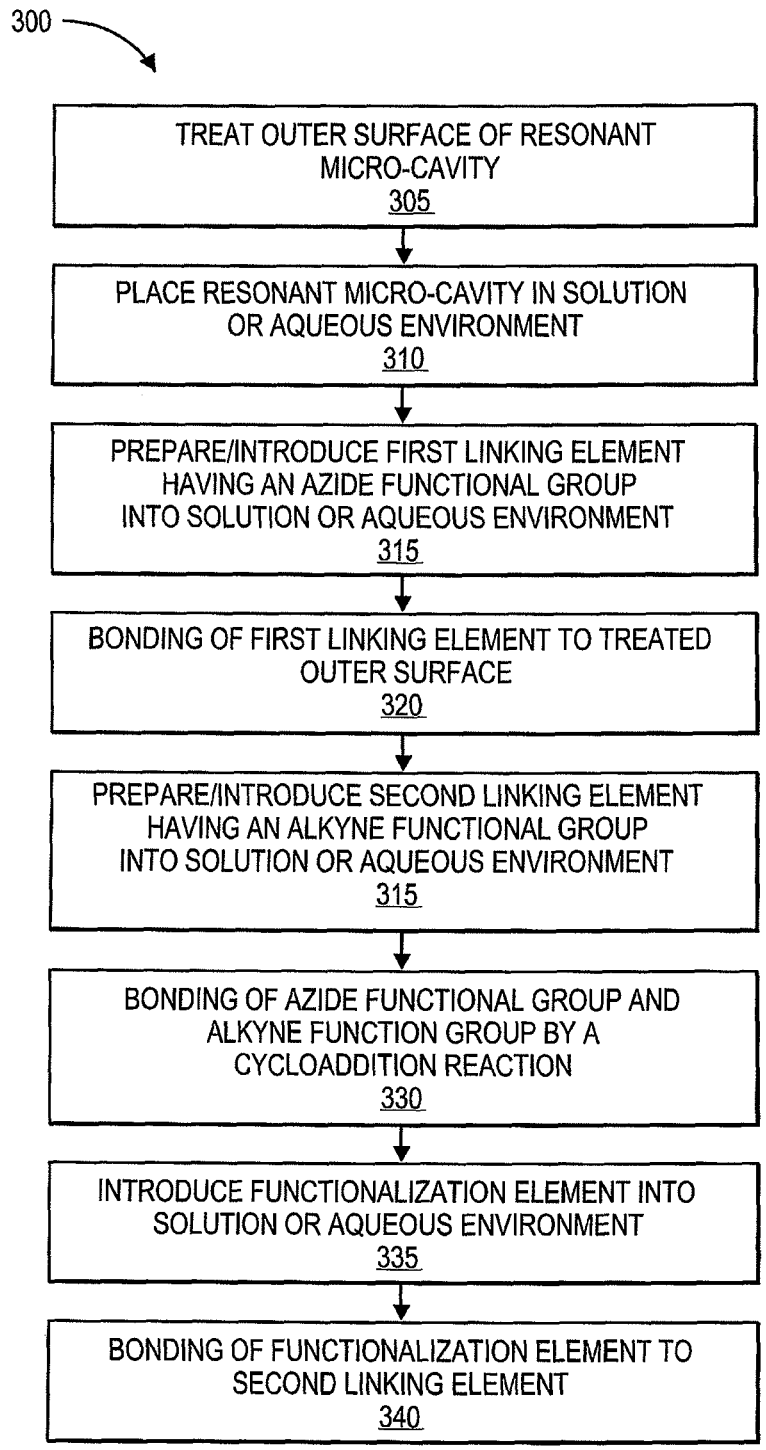
FIG. 3 is a flow chart of a method for functionalizing an outer surface of a resonant micro-cavity using a cycloaddition reaction according to one embodiment.
Figure 4A:
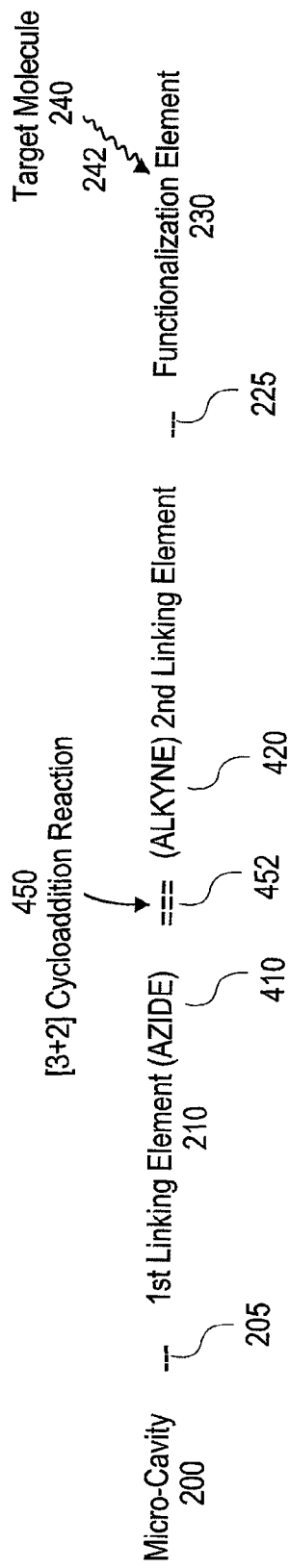
FIG. 4A further illustrates bonding of different components using surface functionalization based on a cycloaddition reaction of an azide functional group and an alkyne functional group according to one embodiment.
Figure 4B:
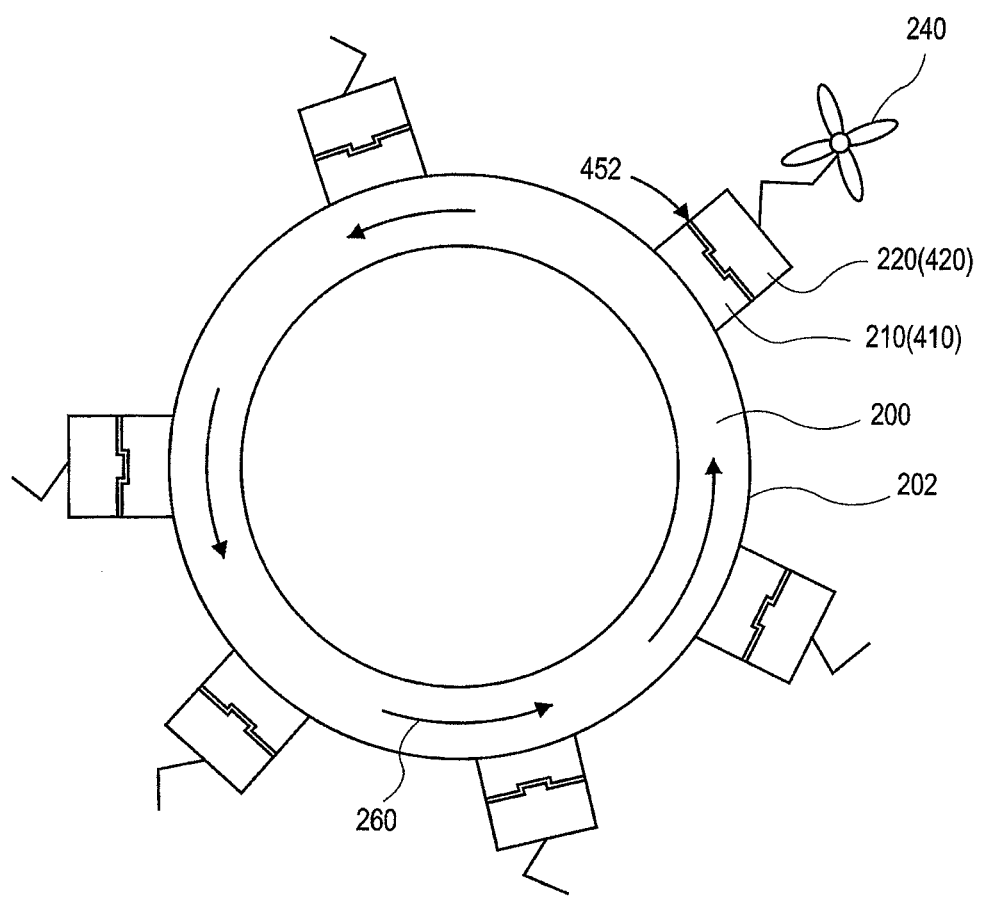
FIG. 4B generally illustrates a top view of a toroid-shaped resonant micro-cavity having an outer surface that is functionalized utilizing a cycloaddition reaction.

Referring to FIG. 3 and with further reference to FIGS. 4A-F, one embodiment of a method 300 for functionalizing or preparing a resonant micro-cavity 200 for use as a sensor utilizing click chemistry 250 involves a [3+2]cycloaddition reaction 450 of an azide functional group 410 of the first linking element 210 that binds to an outer surface 202 of the micro-cavity 200 and an alkyne functional group 420 of the second linking element 220 to which the functionalization element 230 is bound. According to one embodiment, the cycloaddition reaction 450 is a [3+2]cycloaddition reaction. Embodiments may also involve other types of click chemistry 250 reactions including, but not limited to the Diels-Alder [4+2] cylcoaddition reaction between a diene and a dienophile. In this embodiment, a diene bonds to the outer surface 202 while a dienophile is attached to a functionalization element 230 or probing molecule. In the illustrated embodiment, the functionalization method 300 involves treating the outer surface 202 of the resonant micro-cavity 200 in preparation for binding 205 of the first linking element 210 to the outer surface 202 at step 305.

As discussed with reference to FIG. 1, step 305 may involve treating or activating an outer silica surface 202 using a Piranha etch solution. At step 310, the resonant micro-cavity is placed in a solution or aqueous environment. At step 315, the first linking element 210 having the azide functional group 410 is synthesized or prepared (if necessary) and introduced into the solution or aqueous environment in which the resonant micro-cavity 200 is placed. As a result, in step 320, a covalent bond 205 is formed between the first linking element 210 having the azide functional group 410 and the active outer surface 202 of the resonant micro-cavity 200. At step 325, the second linking element 220 having the alkyne functional group 420 is synthesized or prepared (if necessary) and introduced into the solution or aqueous environment. At step 330, a covalent bond 452 is formed between the alkyne functional group 420 and the azide functional group 410 as a result of a [3+2]cycloaddition reaction 450. At step 335, a functionalization element 230 for sensing a target molecule 240 is introduced into the solution or aqueous environment, and at step 340, the functionalization element 230 bonds or is attached 225 to the second linking element 220. FIGS. 4C-F illustrate that embodiments involving a [3+2]cycloaddition reaction 450 may involve a functionalization element 230 that is an antibody (FIG. 4C), an antibody fragment (Fab, Fc) (FIG. 4D); an antigen (FIG. 4E), or a protein (FIG. 4F), and various target molecules 240 may be detected as discussed above.

The manner in which a target molecule 240 attaches or binds 242 to the outer surface 202 via first and second linking elements 210, 220 as described with reference to FIGS. 1-4F provides for improved flexibility to target several different target molecules 240 in an environmentally benign and stable manner. Further, since embodiments utilize covalent bonding, they are very stable, e.g., stable in the presence of temperature and pH changes. Embodiments provide the ability to control environmental conditions to controllably release target molecules 240 from the functionalized outer surface 202. In this manner, surface functionalization embodiments allow a resonant micro-cavity sensor 200 having a functionalized outer surface 202 to be reused for subsequent detection or sensing.

The first and second linking elements 210, 220 can be synthesized using various materials. According to one embodiment, the first linking element 210 and the second linking element 220 are synthesized using the same polymer, and the ends of the polymer are functionalized to synthesize both linking elements 210, 220. According to one embodiment, the polymer used for this purpose has a molecular weight greater than 100, examples of which include polyethylene glycol (PEG), polyethylene oxide (PEO) and other suitable polymers having sufficiently long chain lengths and ends that can be functionalized. For ease of explanation, reference is made to a PEG polymer or a polymer generally, but it should be understood that other polymers having sufficiently long chain lengths can be utilized to synthesize first and second linking elements 210, 220.

In other embodiments, the first and second linking elements 210, 220 are made of different types of polymers. According to one embodiment, the first and second linking elements 210, 220 for use in embodiments described with reference to FIGS. 1-4F are synthesized from a PEG polymer having functionalized ends such that a molecular weight (MW) of a polymer chain of the first linking element 210 is greater than about 300, and a molecular weight of a polymer chain of the second linking element 220 is greater than 1500. Other embodiments may involve other molecular weights that are greater than 100, and molecular weights of 300 and 1500 are provided as examples of how embodiments may be implemented.

In this particular embodiment, the 300 MW first linking element 210 having the azide functional group 410 is covalently bonded 205 to the treated outer surface 202 of the micro-cavity 200, and the alkyne functional group 420 of the 1500 MW second linking element 220 having an attached functionalization element 230 is covalently bonded 452 to the azide functional group 410 via a cycloaddition reaction 450. Embodiments that utilize these types of reactions and covalent bonds provide controlled, irreversible bonding such that only the azide group 410 and the alkyne group 420 bind to each other by click chemistry 250, e.g., a cylcoaddition reaction 450. Thus, the synthesized, non-biological azide group 410 will not bind to other components of a biological solution. Thus, even if alkyne functional groups 420 do not saturate or bind with all of the available azide groups 410, empty or passive azide 410 binding sites remain empty or unbound due to their selective binding. As a result, other biological elements will not bind to these azide sites 410 given the differences in the chemical structures of the azide functional group 410 and biological elements, thereby reducing or eliminating incorrect or inadvertent binding, which may otherwise reduce the effectiveness of the sensor.

Surface functionalization embodiments can be applied to micro-cavities 200 of various shapes, sizes and configurations may be utilized in embodiments and may be made of various materials. In certain embodiments, the outer surface 202 of a semiconductor micro-cavity 200 is functionalized as described above. In a further embodiment, a micro-cavity 200 that is made of an insulator material is functionalized. In certain embodiments, the micro-cavity 200 is made of silicon, silica (as described above with reference to the Piranha silica surface treatment), glass or silicon nitride.

Figure 5:
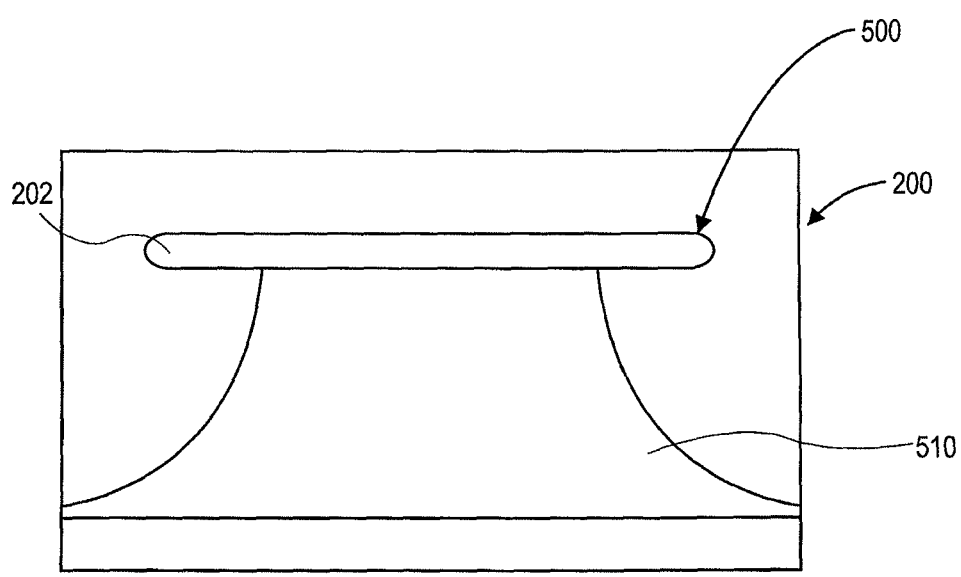
FIG. 5 is a side view of a toroid-shaped resonant microcavity having an outer surface that may be functionalized utilizing click chemistry or a cycloaddition reaction according to embodiments illustrated in FIGS. 1-4F.

Micro-cavities 200 that may be functionalized using click chemistry 250 or a cycloaddition reaction 450 can have a planar shape, e.g., in the form of a disk, a ring or a toroid. For example, FIG. 5 is a scanning electron micro-graph of a planar, toroid-shaped micro-cavity 500, one example of which is described in U.S. application Ser. No. 10/678,354, the contents of which were previously incorporated herein by reference. One suitable toroid-shaped micro-cavity 500 that may be functionalized according to embodiments is made of silica and is supported by a silicon substrate 510. The radius of a toroid-shaped micro-cavity 500 may, for example, be about 15 to 100 micrometers, e.g., about 45 micrometers, and may have high Q values and ultra-high Q values (greater than $10^6$). In the illustrated example, the substrate 510 is tapered such that the micro-cavity 500 in which optical energy 260 resonates extends outwardly beyond the outer edge or top of the substrate 510.

Figure 6:
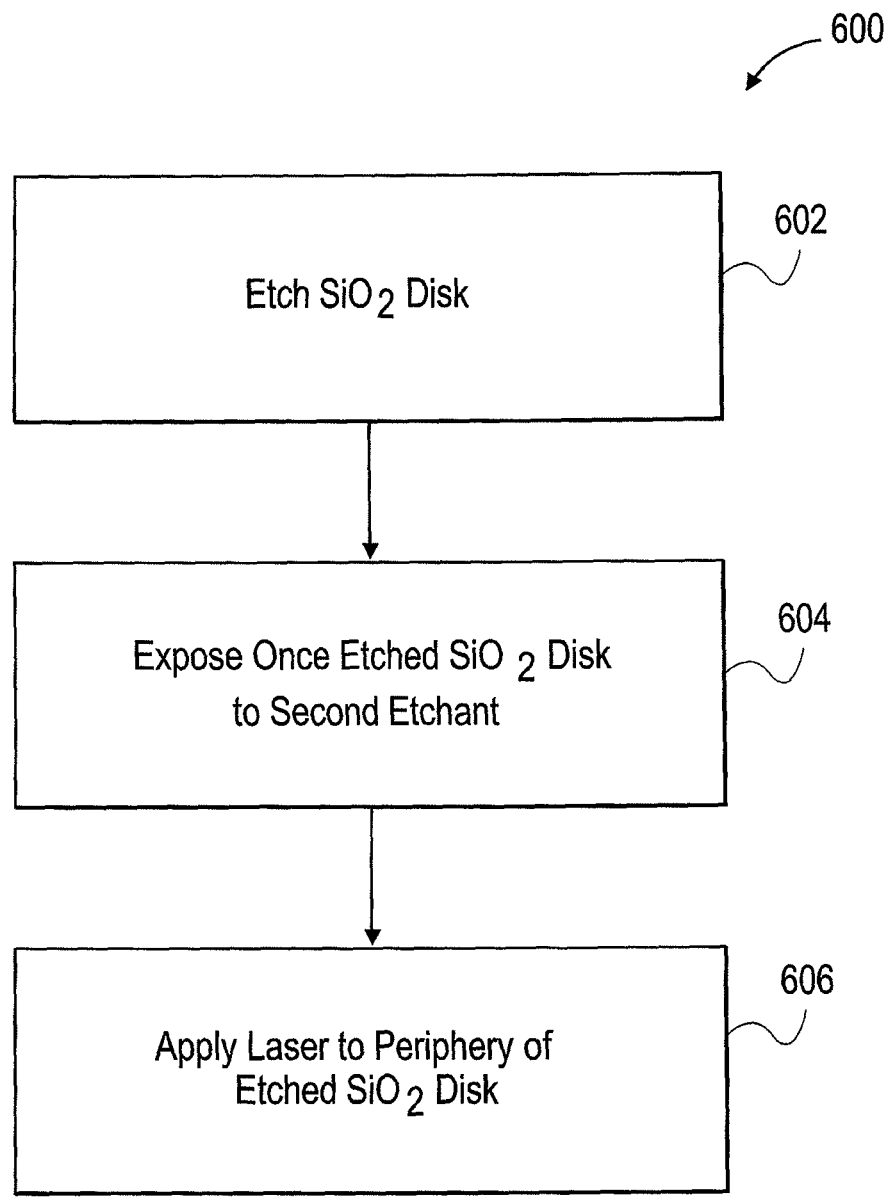
FIG. 6 is a flow diagram illustrating a method of manufacturing a toroid-shaped micro-cavity as shown in FIG. 5.
Figure 7A:
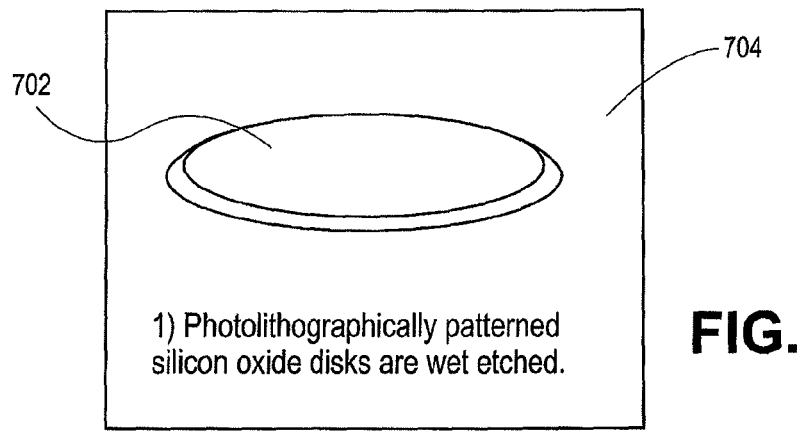
FIGS. 7A-C further illustrate fabrication stages of the method shown in FIG. 6.
Figure 7B:
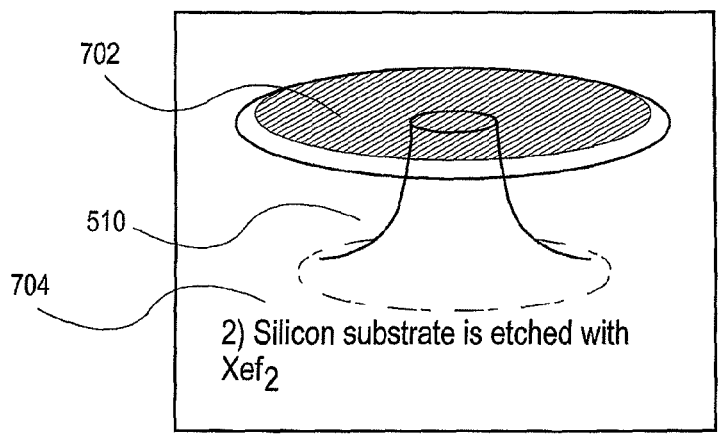
Figure 7C:
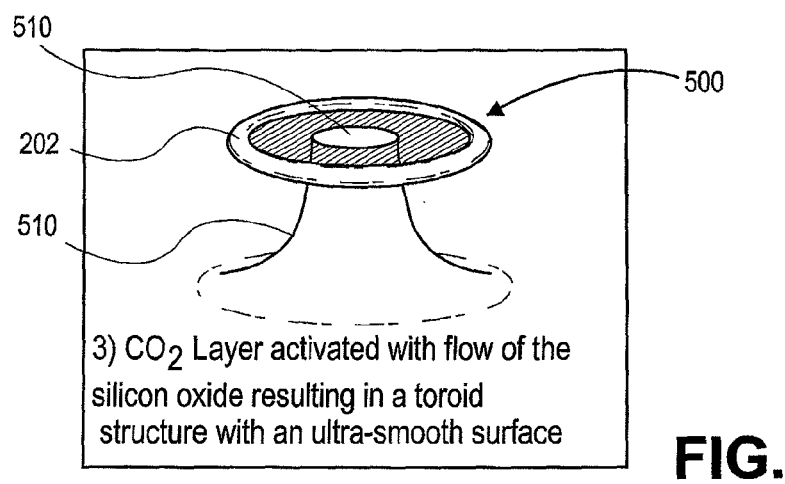

Referring to FIG. 6 and with further reference to FIGS. 7A-C, one method 600 of fabricating a toroid-shaped micro-cavity 500 supported by a substrate 510 as shown in FIG. 5 includes step 602 of wet etching a photolithography patterned silica or silicon dioxide ($SiO_2$) disk or circular pad 702 on a silicon substrate 704 or other suitable substrate (FIG. 7A). This may be done using a hydrogen fluoride (HF) solution or other suitable etchant. In step 604, the silica disk 702 is exposed to a second etchant such as xenon difluoride ($XeF_2$) gas. $XeF_2$ is an etchant with high selectivity that is currently utilized to produce, for example, Micro-Electrical Mechanical Systems (MEMS) devices. $XeF_2$ gas removes or etches portions of the silicon base 704 beneath the periphery of the silica disk 702 (FIG. 6B), thereby forming the tapered silicon support 510. In step 606, a laser, such as an Eximer or $CO_2$ laser, is applied to the undercut periphery of the silica disk 702 (FIG. 7C). As a result, the periphery portions of the silica disk 702 are melted or partially or completely liquefied to reflow and form a toroid-shaped micro-cavity 500 having ultra smooth surfaces (FIGS. 5 and 7C). Further aspects of toroid-shaped micro-cavities 500 and methods of fabrication are described in U.S. application Ser. Nos. 10/678,354 and 11/733,480, the contents of which were previously incorporated herein by reference.

After the micro-cavity 200, such as the toroid-shaped micro-cavity 500 described above, is fabricated, and the outer surface 202 is functionalized by click chemistry 250 or a cycloaddition reaction 450, the outer surface 202 of the micro-cavity 200 is sensitized and ready for detection of target molecules 240 of interest based on changes of optical energy 260 resonating within the micro-cavity 200. Detection of molecules 240 and even detection of a single molecule 240 is accomplished by highly sensitive micro-cavities 200, e.g., having high or ultra-high Q values, that have a very specific outer surface 202 that is functionalized according to embodiments utilizing click chemistry 250 or a cycloaddition reaction 450.

Figure 8:
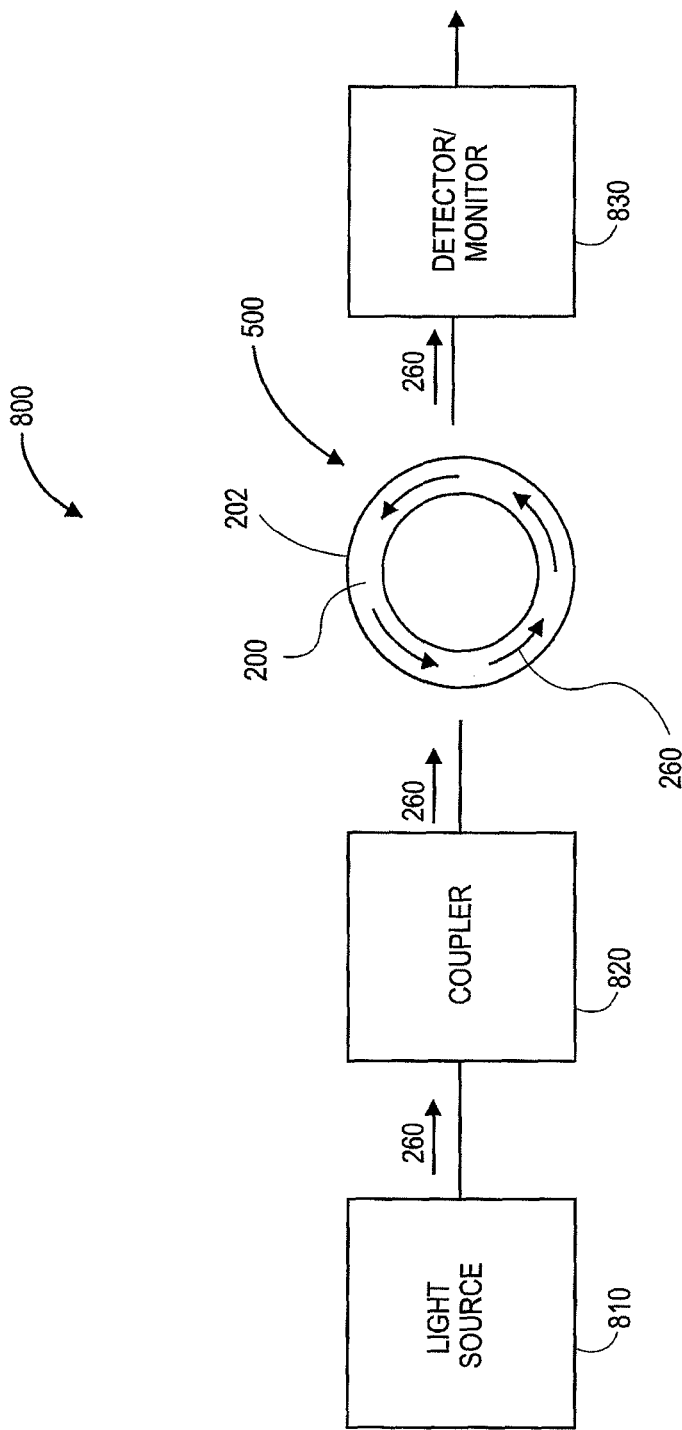
FIG. 8 illustrates a sensor system constructed according to one embodiment that includes a resonant micro-cavity having an outer surface that is functionalized according to embodiments illustrated in FIGS. 1-4F.

Referring again to FIGS. 2A and 4A, and with further reference to FIG. 8, a resonant micro-cavity 200 having a surface 202 functionalized according to embodiments may be part of a sensor system 800. In the illustrated embodiment, the system 800 includes a light source 810, such as a laser, which provides optical energy 260 that is coupled into the micro-cavity 200 via a coupler 820. An optical property of optical energy 260 that evanesces beyond the micro-cavity 200 may be monitored or detected to determine whether a target molecule 240 has bound to the functionalized outer surface 202. More particularly, a resonant micro-cavity 200 having an outer surface 202 functionalized according to embodiments is operable as a sensor based on a change of an optical property of the optical energy 260 resonating within the micro-cavity 200 caused by a target molecule 240 binding 242 to the functionalized outer surface 202.

In the illustrated embodiment, the micro-cavity 200 is a toroid-shaped micro-cavity 500. The wavelength of optical energy 260 may change as a result of one or more molecules 240, and even a single molecule 240, binding 242 to a functionalized outer surface 202 of the micro-cavity 200. Further, when a single molecule 240 or multiple molecules 240 interact with the evanescent field of the optical energy 260, the micro-cavity 200 may be heated, thereby changing the refractive index) of the resonating optical energy 260. In this manner, sensors 200 having an outer surface 202 functionalized according to embodiments can detect small numbers of molecules 240, and even a single molecule 240, without the need to label the target molecule(s) 240 beforehand, as is required in various known single molecule sensors. Changes of other optical properties may also be utilized including, for example, changes of polarization.

Figure 9:
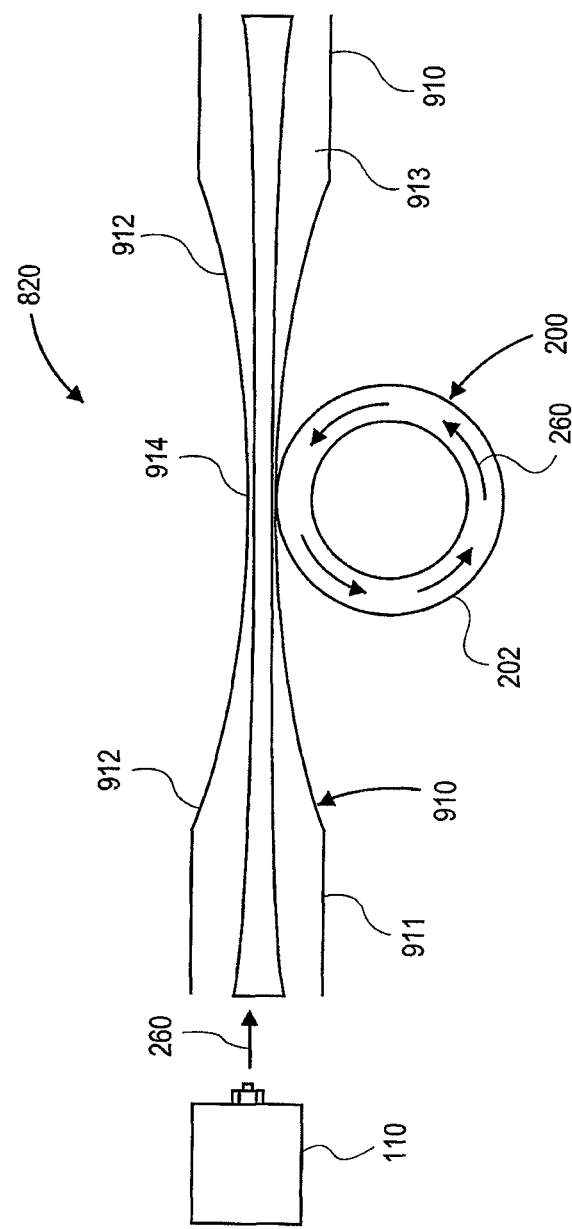
FIG. 9 illustrates an example of a coupler or waveguide in the form of a fiber taper coupler that may be utilized with embodiments.
Figure 10:
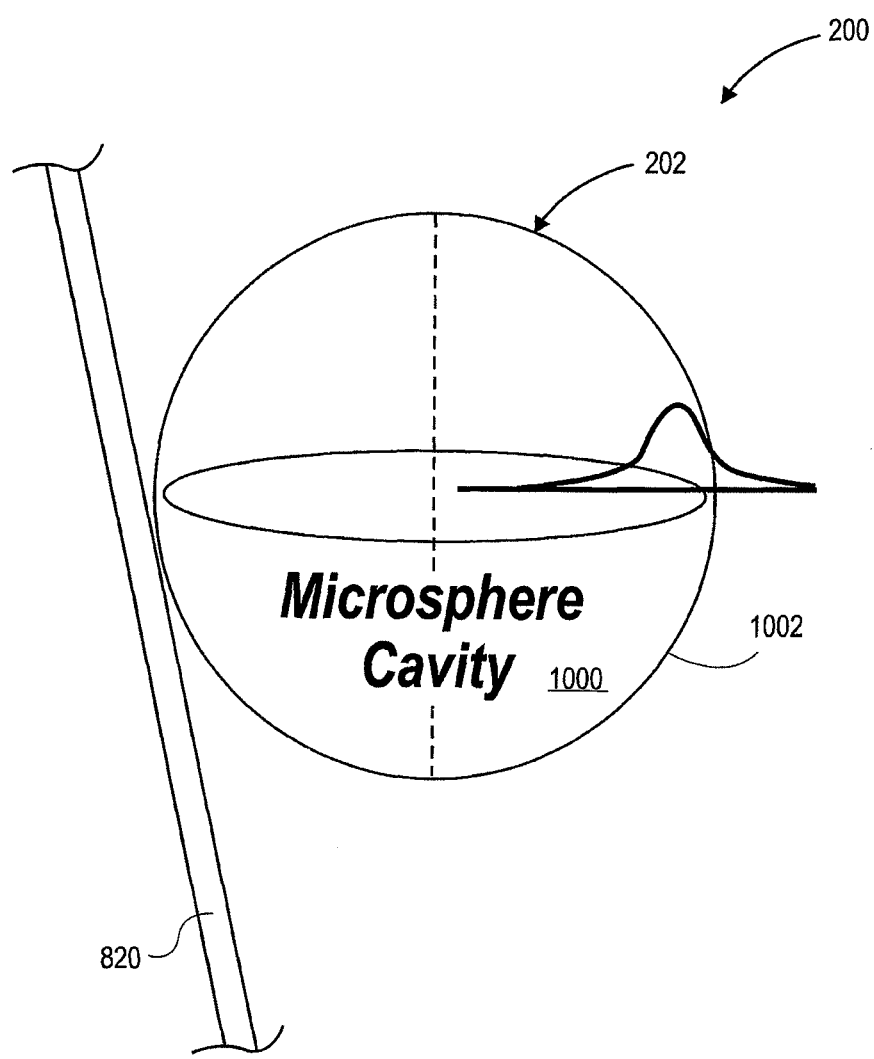
FIG. 10 illustrates a spherical micro-cavity or microsphere having an outer surface that may be functionalized using click chemistry or a cycloaddition reaction according to embodiments illustrated in FIGS. 1-4F.

Referring to FIG. 9, one example of a coupler 820 that may be used in the system 800 shown in FIG. 8 is in the form of a transmission media or fiber coupler 910 that is coupled to a light source or laser 810. Light or optical energy 260 emitted by the laser 810 is coupled into the functionalized micro-cavity 200, e.g., a functionalized toroid-shaped micro-cavity 500 as illustrated, using the fiber coupler 820. In one known coupler 820, the transmission media 910 is a tapered waveguide as shown in FIG. 9, although other waveguide configurations can also be utilized. Tapered sections 912 and the intermediate waist region 914 of the waveguide 910 may be provided, as is known, by stretching a fiber (e.g., a single mode fiber) under controllable tension as it is softened by one or more fixed or movable heat sources (e.g., torches). The diameter of the tapered waist region 914 may be several micrometers, e.g., about 2 micrometers. The toroid-shaped micro-cavity 500, which may be an ultra-high Q micro-cavity, is coupled to the waist region 914 of the fiber 910. The diameter of the waist region 914 can be adjusted to properly phase-match to the toroid-shaped micro-cavity 500.

A light source or optical pump 810 such as a laser is optically connected to a first end 911 of the fiber 910. The optical pump 810 transmits a signal or optical energy 260 along the fiber 910 through the fiber taper 912 and the waist region 914 where it is coupled into the toroid-shaped micro-cavity 500. Evanescent optical energy 260 that emanates from the waist region 914 is coupled into the toroid-shaped micro-cavity 500 such that one or more excited laser signals circulate or resonate within the toroid-shaped micro-cavity 500 with effectively total internal reflection and with minimal internal attenuation and radiative losses, e.g., in a Whispering Gallery Mode (WGM) or other resonant mode. A portion of the resonant optical energy 260 evanesces beyond the micro-cavity 500 and is presented for coupling back into the waveguide waist 914, through an outgoing tapered region 912 and into the outgoing end 913 of the fiber 910. Further aspects of a suitable coupler 900 for use in embodiments are described in U.S. Pat. No. 6,741,628 to Painter et al., the contents of which are incorporated herein by reference.

Although various figures illustrate a single resonant micro-cavity sensor 200 having a single micro-cavity, such as a toroid-shaped micro-cavity 500, other embodiments are directed to an array of resonant micro-cavity sensors 200 that are coupled to one or more or respective couplers 820 or waveguides. An array of sensors 200 may have outer surfaces 202 that are functionalized according to embodiments and the same or different shapes and/or sizes, the same or different resonant wavelengths and may be configured for high throughput detection of multiple gases or vapors. Micro-cavities 200 of an array may be made of the same material or different materials and may include the same or different surface functionalization elements 230. For ease of explanation and illustration, reference is made to an individual resonant micro-cavity sensor 200, but other embodiments may include arrays of various numbers of sensors 200 that can be structured in different manners.

Additionally, although certain embodiments are described with reference to a toroid-shaped micro-cavity 500, sensor embodiments and arrays thereof may also be implemented using micro-cavities 200 of other shapes, sizes, and materials. For example, referring to FIG. 10, a resonant micro-cavity sensor 200 in the form of a spherical micro-cavity or microsphere 1000 may be functionalized using click chemistry 250 or a cycloaddition reaction 450. One example of a microsphere 1000 that may be utilized with surface functionalization embodiments is described in U.S. Pat. No. 6,741,628, the contents of which were previously incorporated herein by reference.

One manner of fabricating a micro-sphere 1000 for use in embodiments involves melting a small piece of glass material, e.g., phosphate glass, in a crucible. While the phosphate is molten, the tip of a silica fiber taper, which has a higher melting point, is placed into the melt. As the silica "stem" is extracted, a small phosphate taper is formed on the end of the silica taper. A laser is used to melt the end of the phosphate taper, forming a sphere under surface tension. The silica fiber stem is finally placed in a fiber chuck and used as a handling rod to control and position the phosphate sphere. The microsphere 1000 may be made of silica and other suitable materials, and may have a diameter of about 100 micrometers to about 3 millimeters, e.g., about 1 millimeter. Other microsphere 1000 materials and dimensions and thicknesses may be utilized, e.g., as discussed above with respect to the toroid-shaped micro-cavity 500. The outer surface 1002 of the micro-sphere 1000 may then be functionalized in a similar manner as described above with reference to FIGS. 1-4F and be integrated into sensor system or within an array of sensors as described above.

Further, the Q value and sensitivity of resonant micro-cavity sensor 200 having a functionalized outer surface 202 according to embodiments can vary and can be configured to detect trace amounts of different target molecules 240 in an aqueous or air environment. For example in certain embodiments, a gas or vapor sensor 200 constructed according to one embodiment having a toroid-shaped micro-cavity 500 has an ultra-high Q value of greater than $10^6$, e.g., $10^7$ and greater than $10^8$. Spherical micro-cavities 1000 may have similar Q values.

FIGS. 11-25B illustrate certain embodiments of first and second linking elements 210, 220, fluorescent counterparts to the linking elements 210, 220 that are synthesized for purposes of testing, and summaries of different fluorescence tests that were performed.

Figure 11:
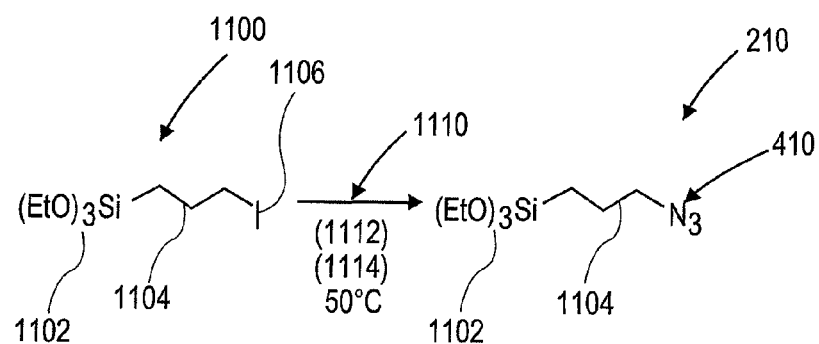
FIG. 11 illustrates synthesis of a first linking element having an azide functional group for use in embodiments.

FIG. 11 illustrates one embodiment of a method for synthesizing a first linking element 210 having an azide functional group 410. In the illustrated embodiment, an initial or starting compound or material 1100 including triethoxysilane ((EtO)$_3$Si) 1102, a polymer such as PEG 1104 and hydrogen 1106 is placed in a solution 1110. According to one embodiment, the solution is a mixture of sodium azide (NaN$_3$) 1112 and dimethylformamide (DMF) 1114 and at a temperature of about 50° C. The resulting reaction of the initial compound 1100 and the solution 1110 leads to synthesis of a first linking element 210. In the illustrated embodiment, the first linking element 210 comprises triethoxysilane ((EtO)$_3$Si) 1102, the polymer (PEG) 1104, and the azide functional group N$_3$ 410.

Figure 12:
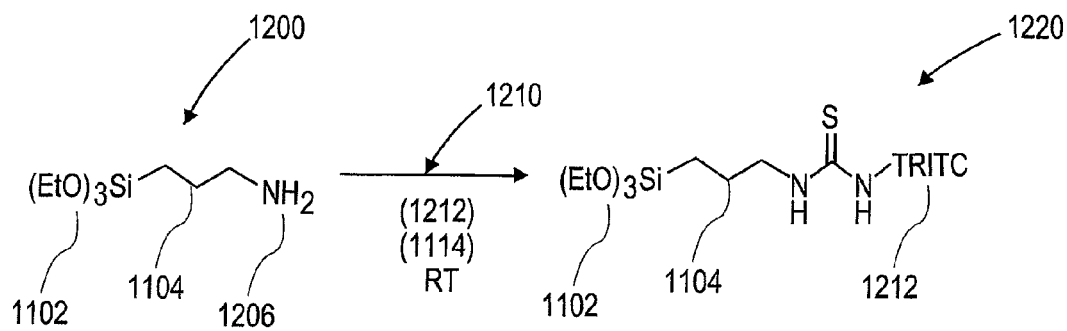
FIG. 12 illustrates synthesis of a fluorescently labeled counterpart to the first linking element shown in FIG. 11 and that is utilized to verify the effectiveness of embodiments.

FIG. 12 illustrates how a fluorescently labeled counterpart 1220 to the first linking element 210 as shown in FIG. 11 can be synthesized for purposes of testing and verifying embodiments. As explained above, embodiments function without the need for labeled molecules, but the fluorescently labeled counterpart 1220 is synthesized for conducting verification tests involving fluorescence intensity as described in further detail below.

Figure 13:
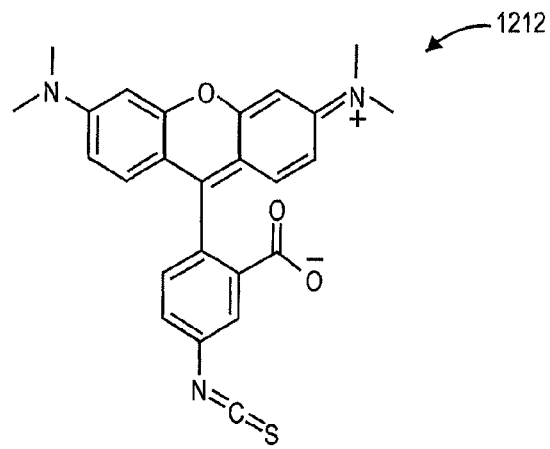
FIG. 13 illustrates a structure of a TRITC molecule of the fluorescently labeled counterpart illustrated in FIG. 12.

In the illustrated example, and with further reference to FIG. 13, an initial or starting compound 1200 including triethoxysilane ((EtO)$_3$Si) 1102, a polymer such as PEG 1104 and NH$_2$ 1206 is placed in a solution 1210 that is a mixture of tetramethyl rhodamine Iso-Thiocyanate (TRITC) 1212 (illustrated in further detail in FIG. 13) and DMF 1114 at room temperature (RT). The resulting reaction of the compound 1200 and the solution 1210 leads to synthesis of a fluorescently labeled counterpart 1220 to the first linking element 210. As shown in FIG. 12, the fluorescently labeled counterpart 12220 includes ((EtO)$_3$Si) 1102, the polymer 1104, TRITC 1212 and associated nitrogen, hydrogen and sulfur elements. TRITC 1212 allows the counterpart 1220 to be used in tests involving analysis of fluorescence intensity.

Figure 14:
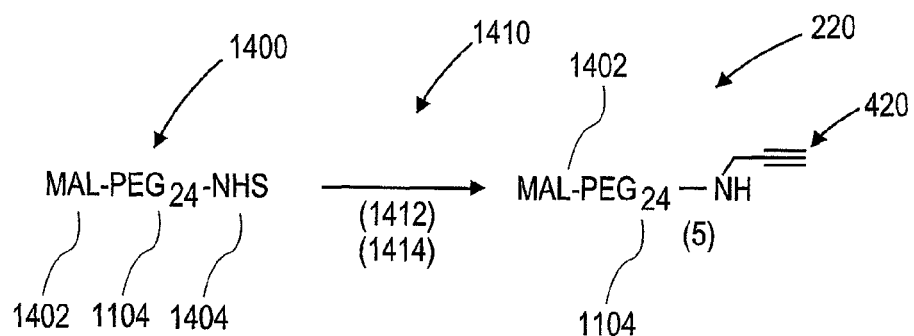
FIG. 14 illustrates synthesis of a second linking element having an alkyne functional group for use in embodiments.
Figure 15:
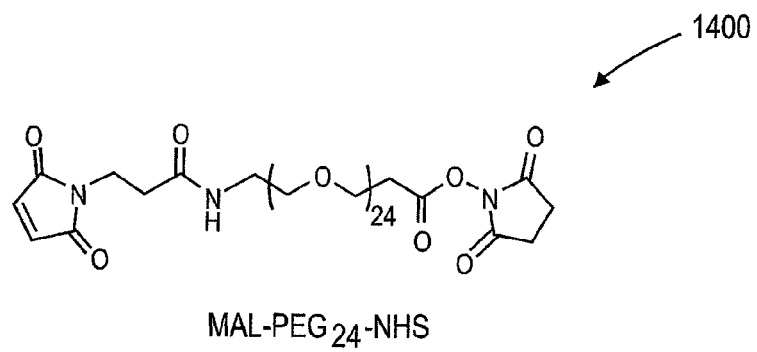
FIG. 15 illustrates the molecular structure of a starting material of the embodiment illustrated in FIG. 14.

FIGS. 14 and 15 illustrate an embodiment of a method for synthesizing a second linking element 220 having an alkyne functional group 420. In the illustrated embodiment, an initial compound 1400 (illustrated in further detail in FIG. 15) including malamite (MAL) 1402, a polymer 1104 such as PEG$_{24}$ or another suitable polymer, and a NHS group 1404 is placed in a solution 1410. In one embodiment, the solution 1410 may be a mixture of propargylamine 1412 and 0.1M sodium bicarbonate (NaHCO$_3$) 1414 at 25° C. The resulting reaction of the compound 1400 and the solution 1410 leads to synthesis of a second linking element 220 including MAL 1402, the polymer 1104 and the alkyne functional group 420. In the embodiments illustrated in FIGS. 11 and 14, the azide functional group 410 of the first linking element 210 and the alkyne functional group 420 of the second linking element 220 bond together by click chemistry 250, e.g. by a cycloaddition reaction 450.

Figure 16:
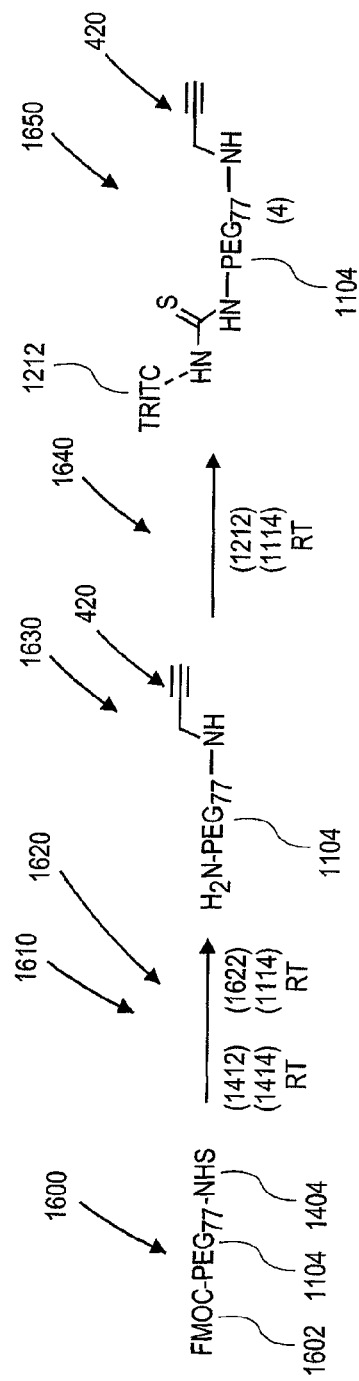
FIG. 16 illustrates synthesis of a fluorescently labeled counterpart to the second linking element shown in FIG. 14 and that is utilized to verify the effectiveness of embodiments.
Figure 17:
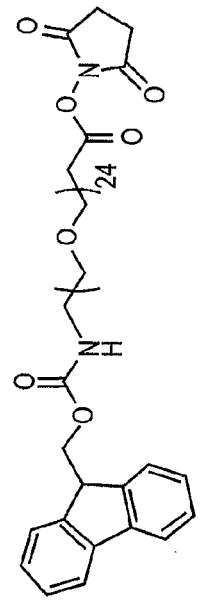
FIG. 17 illustrates the molecular structure of the starting material of the fluorescently labeled counterpart illustrated in FIG. 16.

FIGS. 16 and 17 illustrate how a fluorescently labeled counterpart 1650 to the second linking element 220 as shown in FIG. 14 can be synthesized. As explained above, embodiments are operable without the need for labeled molecules, but the fluorescently labeled counterpart 1650 is synthesized and utilized to verify the effectiveness of embodiments utilizing fluorescence intensity testing, as described in further detail below.

In the illustrated example, an initial compound 1600 (as shown in FIG. 17) including Fluorenylmethoxycarbonyl (FMOC) 1602, a polymer 1104 such as PEG$_{77}$ or another suitable polymer, and a NHS group 1404 is placed in a first solution 1610. The solution 1610 may be a mixture of propargylamine 1412 and 0.1M sodium bicarbonate (NaHCO$_3$) 1414 at room temperature (RT). The compound resulting from that reaction is then placed in a second solution 1620, which is 20% piperidine 1622 in a DMF 1114 solution at room temperature (RT), thereby forming an intermediate compound 1630, which has an alkyne functional group 1632. The intermediate compound 1630 is then placed in a solution 1640 that is a mixture of TRITC 1212 (as shown in FIG. 13) and DMF 1114 at room temperature (RT). The resulting reaction of the intermediate compound 1630 and the solution 1640 leads to synthesis of a fluorescently labeled counterpart 1650 to the second linking element 220. As shown in FIG. 16, the counterpart 1650 includes a polymer 1104, TRITC 1212 for fluorescence studies and the alkyne functional group 420.

Having synthesized the first linking element 210 (FIG. 11), the second linking element 220 (FIG. 14), and their respective fluorescent counterparts 1220, 1650 (FIGS. 12 and 16), the structure of the linking elements 210, 220 was analyzed utilizing nuclear magnetic resonance spectroscopy to verify the structure of the linking elements 210, 220, and which demonstrated that the structure was dominated by a PEG chain. Details of other tests involving the synthesized linking elements 210, 220 and a silica toroid-shaped micro-cavity 500 (as described with reference to FIGS. 5-7C) are described with reference to FIGS. 18-25B.

Figure 18:
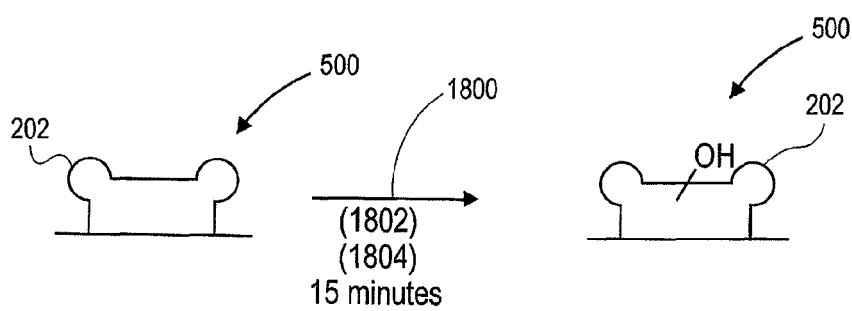
FIG. 18 illustrates treatment of an outer surface of a resonant micro-cavity in preparation for bonding of a fluorescently labeled counterpart to a first linking element to the outer surface.
Figure 19:
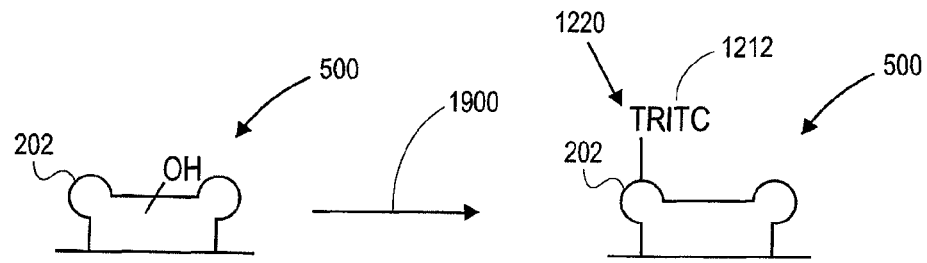
FIG. 19 illustrates bonding of a fluorescently labeled counterpart to a first linking element to an outer surface treated as shown in FIG. 18 for purposes of analyzing the uniformity of bonding of the first linking element to different circumferential positions on the outer surface of the micro-cavity using fluorescence intensity testing.
Figure 20A:
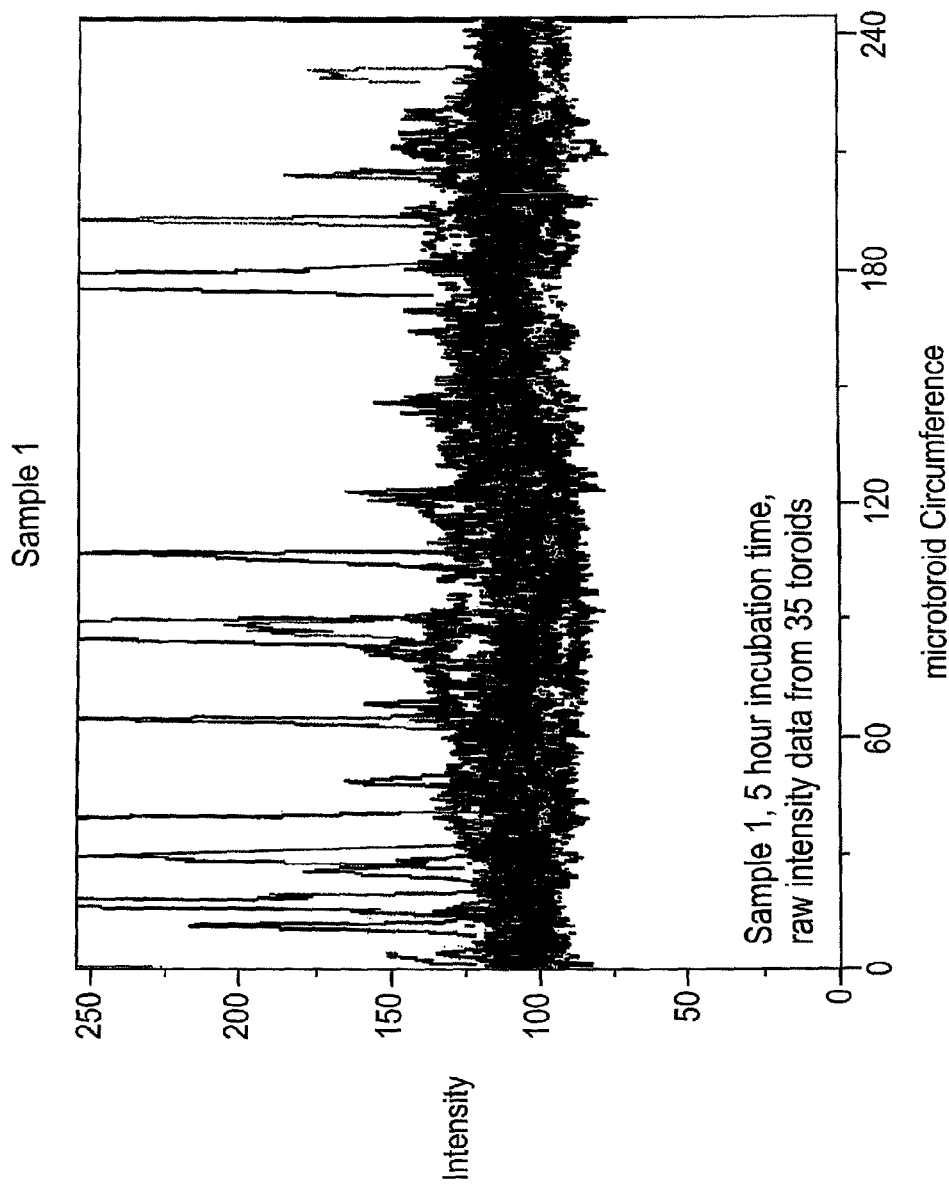
FIGS. 20A-C are graphs illustrating fluorescence intensity test results and data of bonding of fluorescently labeled counterparts to a first linking element as shown in FIG. 19 and that were synthesized using three different methods.
Figure 20B:
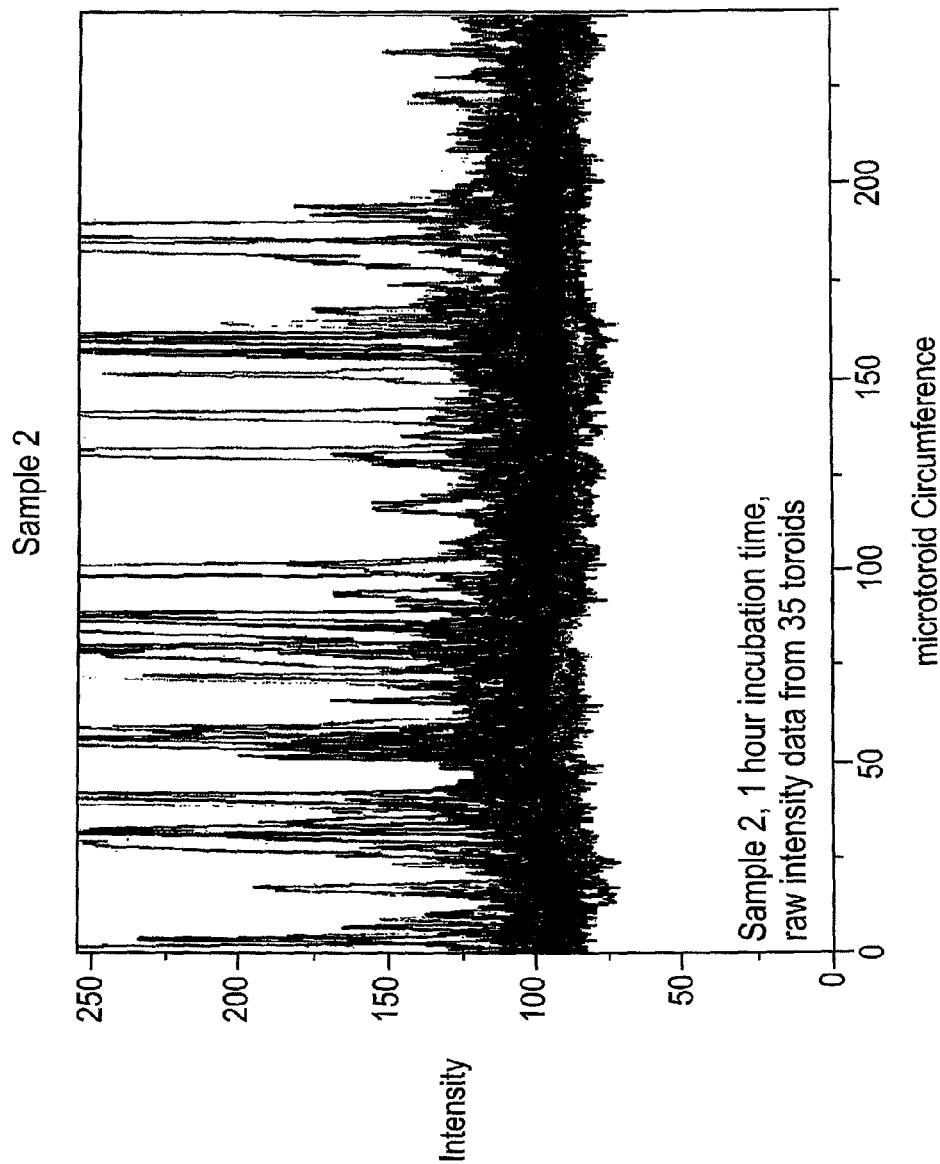
Figure 20C:
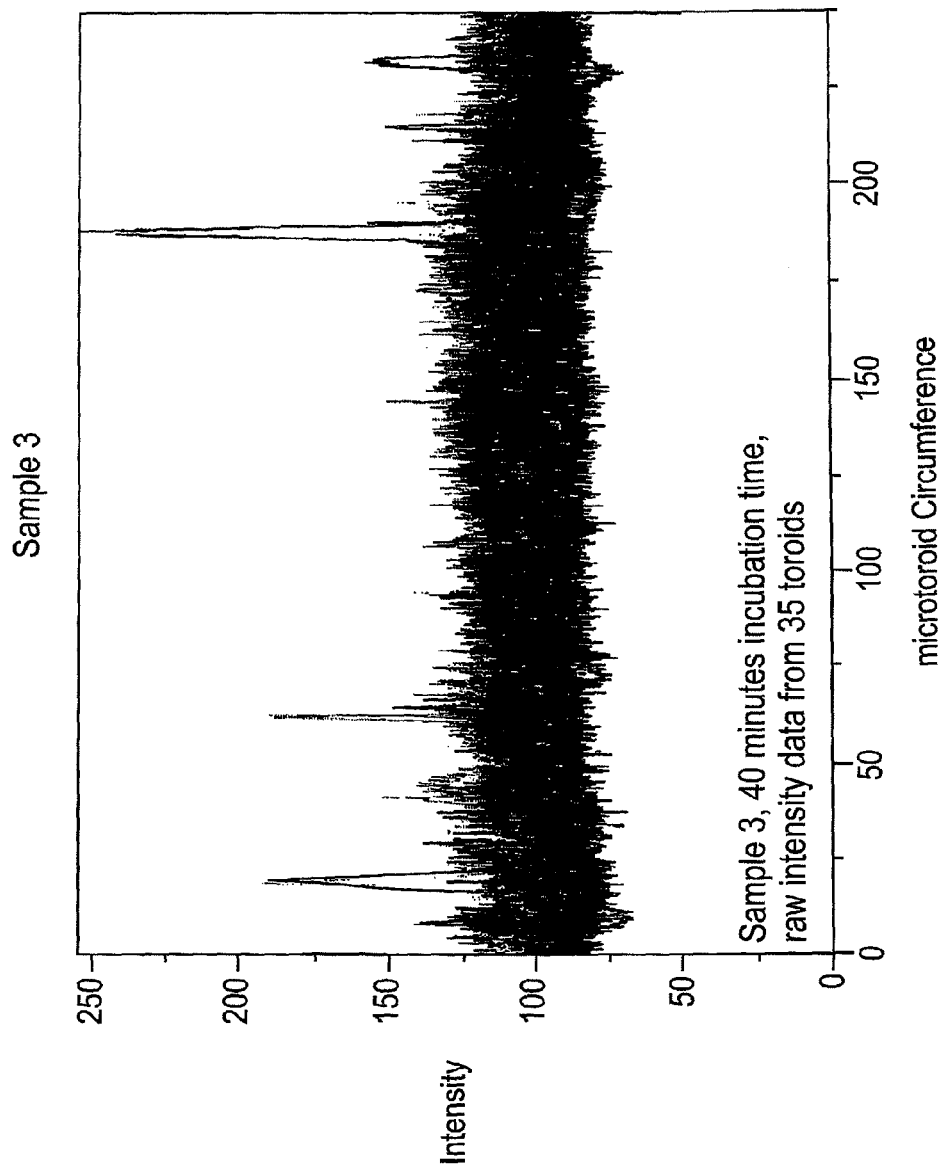

Referring to FIGS. 18-19, to determine acceptable or optimum bonding reaction conditions of the first linking element 210 to the outer silica surface 202 of a toroid-shaped micro-cavity 500, the outer surfaces 202 of three groups of toroid-shaped micro-cavities 500 were treated using a Piranha etch solution of 70% sulfuric acid ($H_2SO_4$) (1802) and 30% hydrogen peroxide ($H_2O_2$) (1804) for about 15 minutes. Samples of the florescent counterpart 1220 (FIG. 12) to the first linking element 210 were prepared. Following the etch treatment 1800, the fluorescent counterpart 1220 to the first linking element 210 was bound to the treated outer surface 202 by placing the treated micro-cavities 500 in a solution 1110 that is a mixture of sodium azide ($NaN_3$) 1112 and DMF 1114 for different lengths of time.

More particularly, a first sample or group of 35 micro-cavities 500 was prepared by binding a fluorescent counterpart 1220 to the first linking element 210 to the outer surface 202 of the toroid-shaped micro-cavities 500 by placing them in solution 1110 having a concentration of about 5 mg/ml and a temperature of about 50° C. for about 5 hours. A second sample or group of 35 micro-cavities 500 was placed in a solution 1110 having a concentration of about 5 mg/ml and a temperature of about 50° C. for about 1 hour. A third sample or group of 35 micro-cavities 500 was placed in a solution 1110 having a concentration of about 5 mg/ml and a temperature of about 50° C. for about 40 minutes.

FIGS. 20A-C and 21A-C graphically illustrate data resulting from measuring the fluorescence intensity along different positions (microns) on the circumference of the outer surface 202 of each micro-cavity 500 in each of the three groups prepared as described above. The fluorescence data for the first group (5 hours in solution 1110) are plotted in FIGS. 20A and 21A, the fluorescence data for the second group (1 hour in solution 1110) are plotted in FIGS. 20B and 21B, and the fluorescence data for the third group (40 minutes in solution 1110) are plotted in FIGS. 20C and 21C. As shown in these figures, the toroid-shaped micro-cavities 500 fabricated using a solution time of 40 minutes (FIGS. 20C and 21C) exhibited the least amount of noise or variance, thus demonstrating that these method parameters resulted in the most uniform binding of the fluorescent counterpart 1220 of the first linking element 210 to the outer surface 202 of the micro-cavity 500. Based on these results, it can be inferred that a similar method can be used for uniform binding of the first linking element 210 to the outer surface 202 of a micro-cavity 200, including a toroid-shaped micro-cavity 500. More particularly, referring to FIGS. 20A-C, clumps, i.e., oligomeric TRITC-silanes or locally π-stacked TRITC 1212, can be reduced using shorter reaction times (e.g., about 40 minutes in solution rather than 1 or 5 hours), and FIGS. 21A-C illustrate that the geometric means around the toroid-shaped micro-cavity 500 show a minimal intensity variation over the entire toroid surface 202 from sample to sample, and that longer reaction times and higher concentrations may not provide significant advantages.

Figure 22:
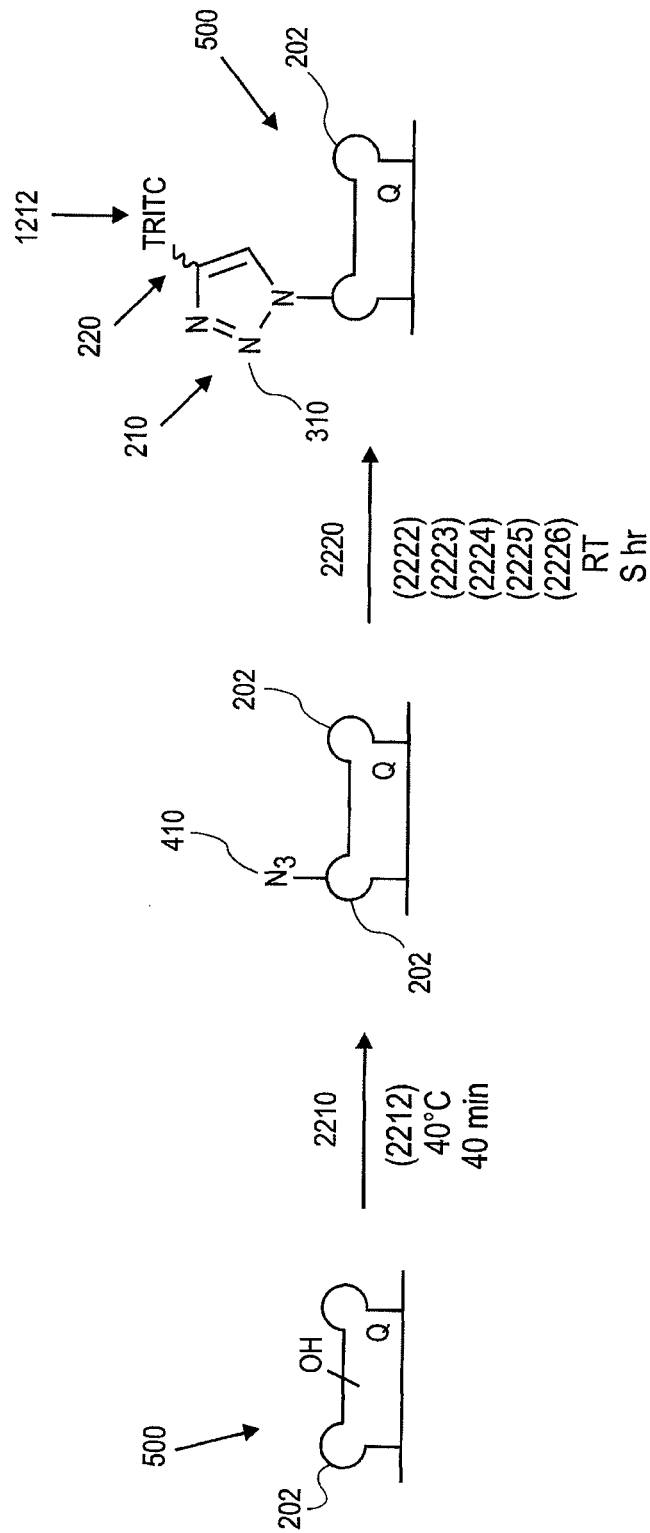
FIG. 22 illustrates a fluorescently labeled counterpart to embodiments having first and second linking elements for purposes of analyzing the uniformity of bonding of the first and second linking elements to different circumferential positions on the outer surface of the micro-cavity using fluorescence intensity testing.

Referring to FIG. 22, additional experiments were performed to check for auto-fluorescence of toroid-shaped micro-cavity 500 samples prepared to having both of the first and second linking elements 210, 220 rather than only the first linking element 210 and possible binding without catalysts. As shown in FIG. 22, an outer surface 202 of a toroid-shaped micro-cavity 500 was treated using a Piranha etch solution as described above to activate the outer surface 202. The micro-cavity 500 was placed in a solution 2210 having 0.5 mg/ml concentration of EtOH 2212 at 40° C. for about 40 minutes, thereby resulting in bonding of a first linking element 210 having an azide functional group ($N_3$) 410 to the outer surface 202 of the micro-cavity 500. The micro-cavity 500 having the azide functional group 410 was then placed in a solution 2220 containing copper sulfate ($CuSO_4$) 2222, tris(2-carboxyethyl)phosphine) (TCEP) 2223, a solvent tert-butyl alcohol (t-BuOH) 2224. 50 mM lead sulfide 2225 and tristriazolylamine 2 mM in a dimethyl sulfoxide (DMSO) 2226 solvent at room temperature (RT) for about five hours. The click reaction 250 may also be controlled without copper sulfate (CuSO4), TCEP and tristriazolylamine. For example, the solution utilized may include t-BuOH, PBS 50 mM at room temperature for 5 hours.

The reaction of the treated outer surface 202 and the solution 2220 results in a click chemistry 250 or cylcoaddition reaction 450 such that the a molecular structure including the first linking element 210 having the azide functional group ($N_3$) 410, a second linking element 220 having an alkyne functional group 420 and a TRITC molecule 1212. During this test, TRITC 1212 was introduced after applying the first linking element 210 and after applying the second linking element 220. As a result, at each of these points, TRITC 1212 was introduced such that the end groups of the linking elements 210, 220 were replaced with TRITC 1212, thereby resulting in the molecular structure shown in FIG. 22 in which TRITC 1212 replaces an end group of the alkyne functional group 420 for use in fluorescence testing to demonstrate the effectiveness of embodiments.

Figure 23B:
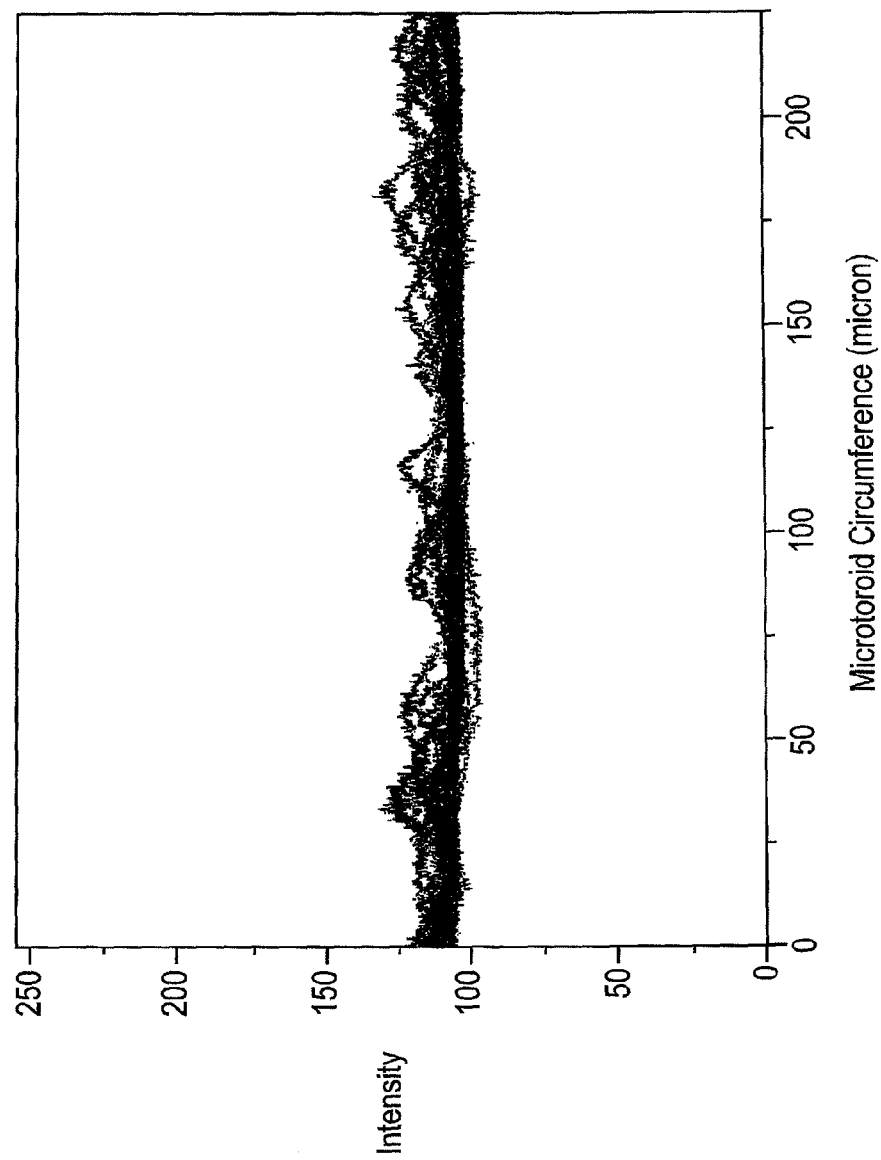
Figure 23C:
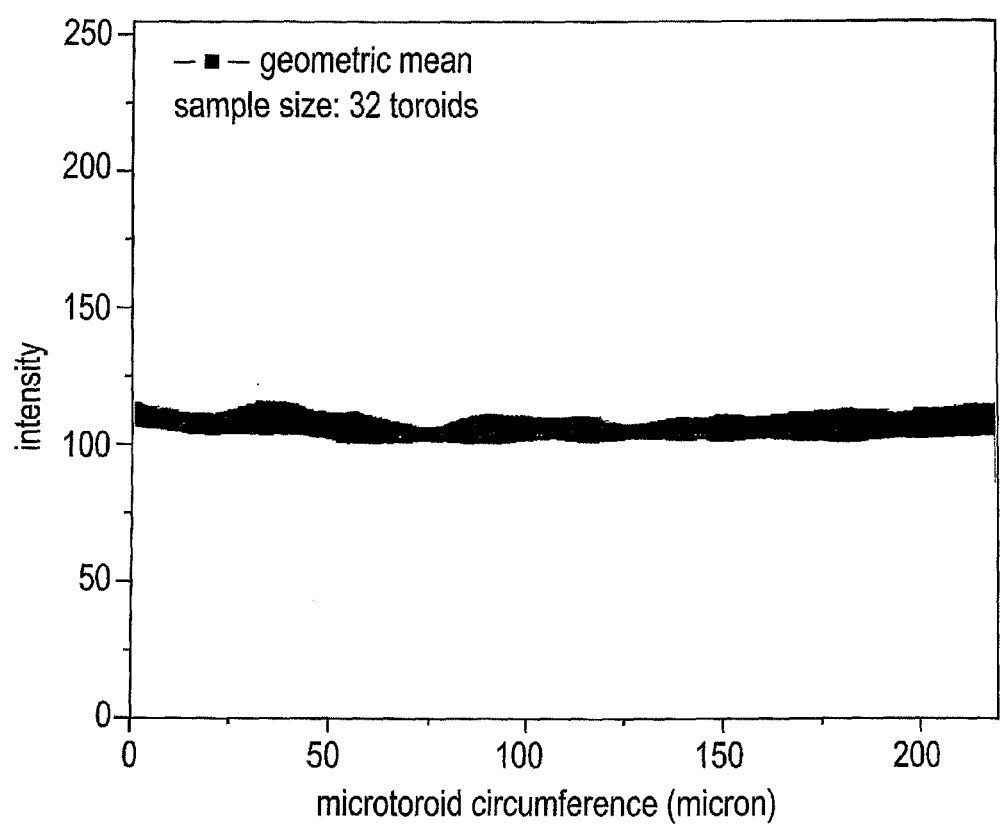

FIGS. 23A-C are graphs of data illustrating fluorescence intensity relative to a circumferential position along an outer surface 202 of the toroid-shaped micro-cavity 500 that is functionalized using both first and second linking elements 210, 220 and click chemistry 250. FIG. 23A illustrates raw fluorescence intensity data relative to a circumferential position along the outer surface 202. FIG. 23B illustrates the data shown in FIG. 23A but with clumps, micelles, or spheres of molecules removed from the outer surface 202, thereby demonstrating uniformity based on the presence of minimal micelles on the outer surface 202. FIG. 23C illustrates the geometric mean of the fluorescence intensity relative to the circumferential position along the outer surface 202. The geometric mean data shown in FIG. 23C illustrates minimal intensity variation over the entire outer circumferential surface 202.

Figure 24:
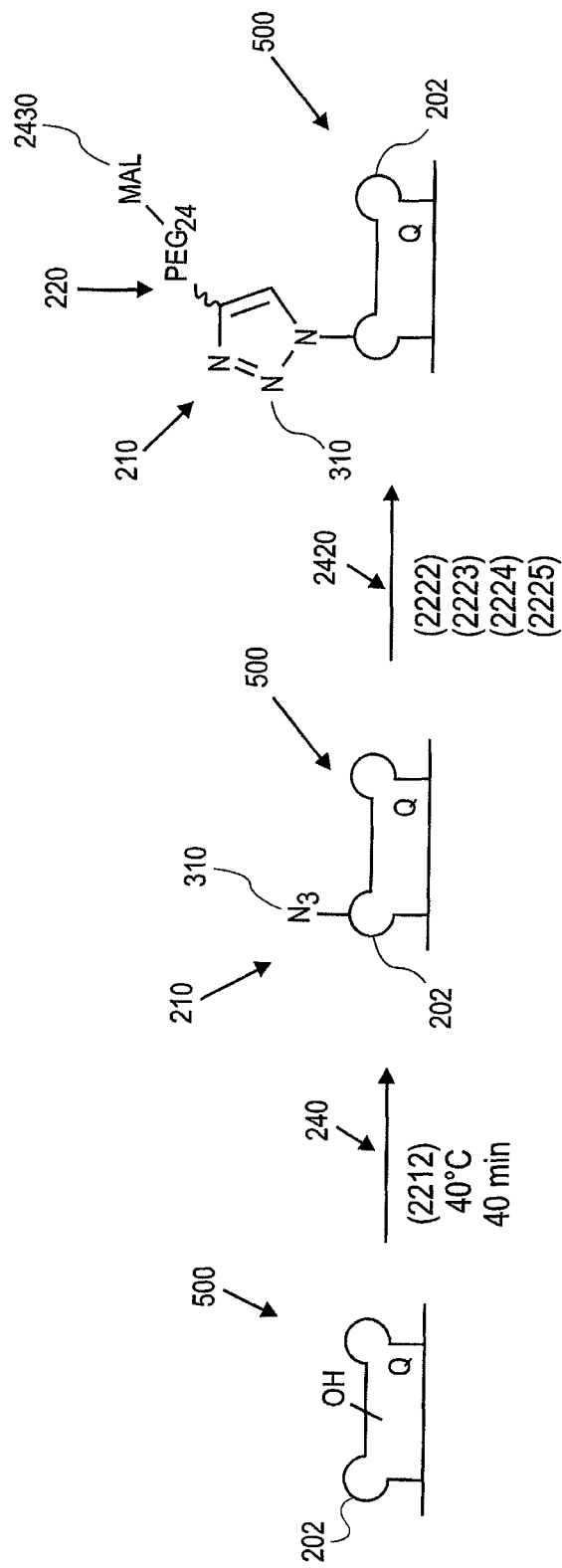
FIG. 24 illustrates bonding of first and second linking elements to an outer surface of a micro-cavity and bonding of malamite for use in binding to functionalization elements.
Figure 25A:
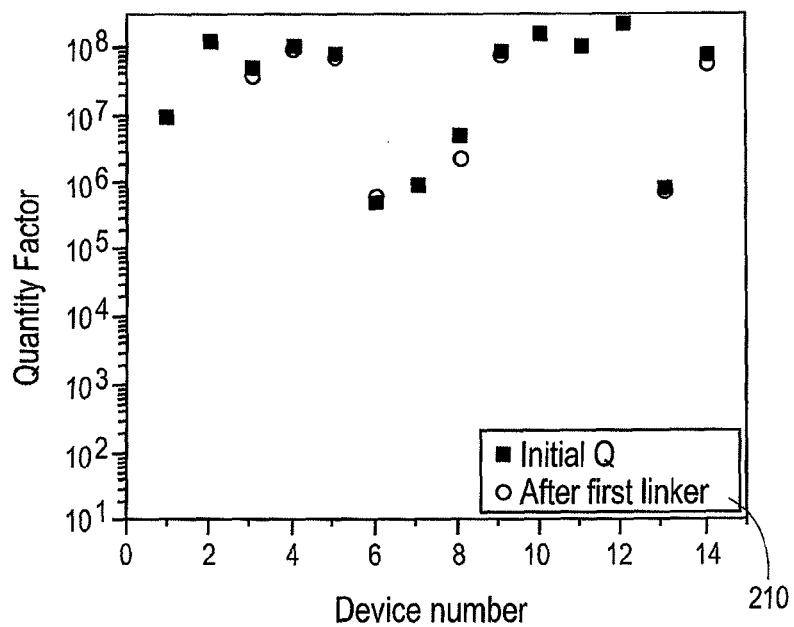
Figure 25B:
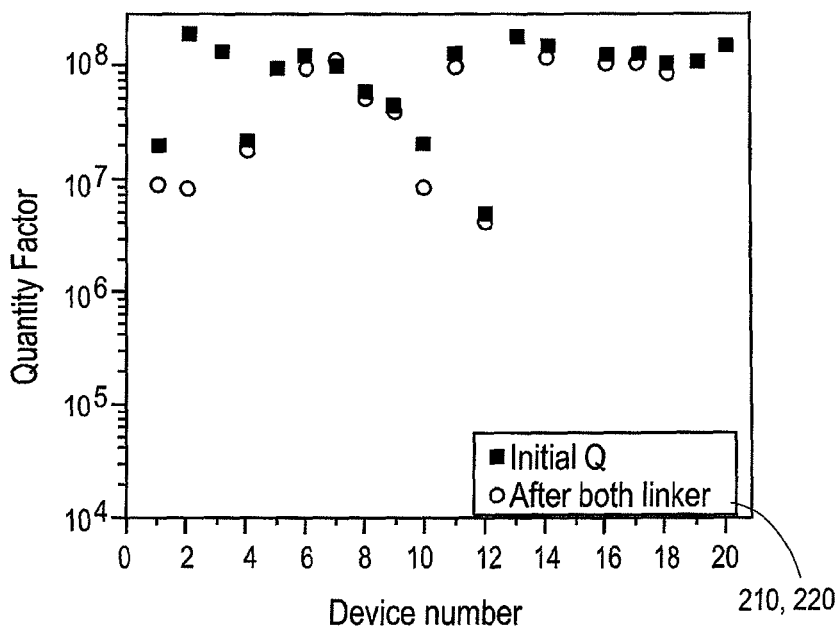

Referring to FIGS. 24-25B, another test involved analyzing the quality (Q) factor of optical energy 260 resonating within a toroid-shaped micro-cavity 500 functionalized with both first and second linking elements 210, 220 and malamite (MAL) 2430, to which functionalization elements 230 can be attached. Tests were performed using micro-cavity 500 functionalized as shown in FIG. 24 to verify that the first and second linking elements 210, 220 do not negatively impact Q factor or do so to a negligible or acceptable degree.

Referring to FIG. 24, outer surfaces 202 of multiple toroid-shaped micro-cavities 500 were treated using a Piranha etch solution and then placed in a solution 2410 having 0.5 mg/ml concentration of EtOH 2212 at 40° C. for about 40 minutes, thereby resulting in bonding of the first linking element 210 having an azide functional group ($N_3$) 410 to the outer surfaces 202 of the micro-cavities 500. The micro-cavities 500 having the first linking element 210 were then placed in a solution 2420 containing copper sulfate ($CuSO_4$) 2222, tris (2-carboxyethyl)phosphine) (TCEP) 2223, a solvent tert-butyl alcohol (t-BuOH) 2224, 50 mM lead sulfide 2225 and tristriazolylamine 2 mM in a dimethyl sulfoxide (DMSO) 2226 solvent at room temperature (RT) for about five hours, as described above with reference to FIG. 22. The reaction of the solution 2420 and the treated outer surfaces 202 having the first linking element 210 resulted in a click chemistry 250 or cylcoaddition reaction 450 of the azide functional group ($N_3$) 410 of the first linking element 210 and the alkyne functional group 420 of the second linking element 220, which is mixed in the reaction with the solution 2220 to form a TRITC 1212 labeled counterpart 1650 linked to the first linking element 210 via cyclic ring. Alternatively, the reaction may be carried out without copper sulfate ($CuSO_4$), TCEP and tristriazolylamine. For example, the solution 2420 utilized may include t-BuOH, PBS 50 mM at room temperature for 5 hours. Malamite (MAL) 2430 is attached to the second linking element 220, in a manner that is similar to how a functionalization element 230 for sensing a target molecule 240 would be attached to the second linking element 220.

FIGS. 25A-B are graphs plotting Q factor data for the micro-cavities functionalized as shown in FIG. 24. FIG. 25A illustrates Q factor data for a toroid-shaped micro-cavity 500 after binding of the first linking element 210 to the outer surface 202. FIG. 25B illustrates Q factor data for a toroid-shaped micro-cavity 500 after binding of the second linking element 220 to the first linking element 210.

As shown in FIGS. 25A-B, the Q factor is not impacted, or is impacted by a small amount, thereby demonstrating that surface functionalization embodiments do not impact Q factor or do so to a minimal or negligible degree. More particularly, it was determined that the average reduction of Q factor upon addition of the first linking element 210 to the outer surface 202 was about 15%, and the combined average Q factor reduction upon binding of the second linking element 220 was about 20%. The smallest Q factor reduction that was observed was about 2% Thus, these experiments demonstrated the effectiveness of embodiments and that embodiments are useful for functionalizing outer surfaces of high Q and ultra-high Q micro-cavities.

Although references have been made in the foregoing description to various embodiments, persons of ordinary skill in the art will recognize that insubstantial modifications, alterations, and substitutions can be made to the described embodiments without departing from the invention as recited in the accompanying claims.

For example, embodiments may involve resonant micro-cavities that are made of various resonator materials and may have various shapes and sizes. Further, arrays of sensors may have various numbers of sensors, which may have the same or different micro-cavities and deformable coatings. Embodiments may involve various types of functionalization elements to detect certain target molecules.

Additionally, various surface treatments may be used to activate the outer surface for binding of the first linking element. The linking elements may also be formed or made from various polymers, which may be the same or different polymers. Polymers of various molecular weights may be utilized. Synthesis parameters may also be adjusted as necessary. Further, various types of click chemistry and cylcoaddition reactions may be utilized. Additionally, various types of bonds or linkages may be formed between a second linking element and a functionalization element, which may be used to detect various types of target molecules, including single molecules.

Moreover, in other embodiments, an outer surface of a micro-cavity can be partially functionalized (e.g., 75% functionalized), and after a target molecule is identified, the remaining surface can be functionalized for a later identified target molecule.

Additionally, where methods and steps described above indicate certain events occurring in certain order, it should be understood upon reading this disclosure that the ordering of certain steps may be modified and that such modifications are in accordance with the variations of the invention. Certain steps may be performed concurrently in a parallel or performed sequentially as described above. For example, although embodiments are describe with reference to a sequence of a first linking element bonding to a resonator surface, a second linking element bonding to the first linking element, and a functionalization element bonding to the second linking element, other embodiments involve binding of the functionalization element to the second linking element, and then binding of the second linking element to the first linking element, before or after the first linking element binds to the outer surface of the micro-resonator. Accordingly, it should be understood that the sequence of steps illustrated in various figures are provided for purposes of explanation and illustration and in a non-limiting manner, and that various steps and reactions may occur in different orders.

Thus, it should be understood that the invention generally, as well as the specific embodiments described herein, are not limited to the particular forms or methods disclosed, but also cover all modifications, equivalents and alternatives falling within the scope of the appended claims.

What is claimed is:

1. A resonant micro-cavity sensor, comprising:
   a resonant micro-cavity having an outer surface and a Q factor greater than $10^8$;
   a first polymer linking element bound to the outer surface;
   a second polymer linking element bound to the first linking element by click chemistry and
   a functionalization element for sensing a target molecule, the functionalization element being bound to the second linking element.

2. The sensor of claim 1, wherein the functionalization element is an antibody, an antibody fragment, an antigen or a protein.

3. The sensor of claim 1, wherein the first polymer linking element and the second polymer linking element form a substantially uniform single layer.

4. The sensor of claim 1, wherein respective polymer chains of the first polymer linking element and the second polymer linking element have respective molecular weights greater than 100.

5. The sensor of claim 1, wherein a molecular weight of a polymer chain of the first polymer linking element is greater than about 300, and a molecular weight of a polymer chain of the second polymer linking element is greater than 1500.

6. The sensor of claim 1, wherein the resonant micro-cavity is a planar micro-cavity.

7. A resonant micro-cavity sensor, comprising:
   a resonant micro-cavity having an outer surface and a Q factor greater than $10^8$;
   a first polymer linking element bound to the outer surface and having a first functional group;

a second polymer linking element having a second functional group, wherein a bond is formed between the first functional group and the second functional group as a result of a cycloaddition reaction, and a functionalization element for detecting a target molecule, wherein the functionalization element is bound to the second linking element.

8. The sensor of claim 7, wherein the functionalization element is an antibody, an antibody fragment, an antigen or a protein.

9. The sensor of claim 7, wherein the first polymer linking element and the second polymer linking element form a substantially uniform single layer.

10. The sensor of claim 7, at least one of the first linking polymer element and the second polymer linking element is made of a polyethylene glycol polymer.

11. The sensor of claim 7, wherein the first polymer linking element and the second polymer linking element have respective polymer chains of respective molecular weights greater than 100.

12. The sensor of claim 10, wherein a molecular weight of a polymer chain of the first polymer linking element is greater than about 300, and a molecular weight of a polymer chain of the second polymer linking element is greater than 1500.

13. The sensor of claim 7, wherein a covalent bond is formed between the first functional group and the second functional group.

14. The sensor of claim 7, wherein the first polymer linking element and the second polymer linking elements are bonded to each other by a cycloaddition reaction of an azide group of the first polymer linking element and an alkyne group of the second polymer linking element.

15. A resonant micro-cavity sensor, comprising:

a resonant micro-cavity having an outer surface and a Q factor greater $10^8$;

a first polymer linking element bound to the outer surface and having an azide functional group, a polymer chain of the first polymer linking element having a molecular weight greater than 100;

a second polymer linking element having alkyne functional group, wherein a bond is formed between the azide functional group and the alkyne functional group as a result of a cycloaddition reaction, a polymer chain of the second polymer linking element having a molecular weight greater than 100; and a functionalization element for detecting a target molecule, wherein the functionalization element is bound to the second polymer linking element.

16. The sensor of claim 15, wherein the functionalization element is an antibody, an antibody fragment, an antigen or a protein.

17. The sensor of claim 15, wherein the molecular weight of a polymer chain of the first polymer linking element is greater than about 300, and the molecular weight of a polymer chain of the second polymer linking element is greater than 1500.

18. The sensor of claim 1, at least one of the first linking polymer element and the second polymer linking element comprising a polyethylene glycol polymer, wherein a molecular weight of a polymer chain of the first linking element is at least 300, and a molecular weight of a polymer chain of the second polymer linking element is at least 1500.

19. The sensor of claim 15, at least one of the first linking polymer element and the second polymer linking element comprising a polyethylene glycol polymer.

20. The sensor of claim 1, at least one of the first linking polymer element and the second polymer linking element comprising a polyethylene oxide polymer.

21. The sensor of claim 15, at least one of the first linking polymer element and the second polymer linking element comprising a polyethylene oxide polymer.

* * * * *